United States Patent
Nishigaki et al.

(10) Patent No.: US 6,794,509 B1
(45) Date of Patent: Sep. 21, 2004

(54) COMPOUNDS FOR FLUORESCENCE LABELING

(75) Inventors: Junji Nishigaki, Minami-ashigara (JP); Kouki Nakamura, Minami-ashigara (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 10/088,232

(22) PCT Filed: Sep. 20, 2000

(86) PCT No.: PCT/JP00/06401

§ 371 (c)(1),
(2), (4) Date: Jul. 17, 2002

(87) PCT Pub. No.: WO01/21624

PCT Pub. Date: Mar. 29, 2001

(30) Foreign Application Priority Data

| Sep. 20, 1999 | (JP) | 11-264844 |
| Sep. 20, 1999 | (JP) | 11-264845 |
| Oct. 18, 1999 | (JP) | 11-294910 |
| Oct. 18, 1999 | (JP) | 11-294911 |
| Apr. 19, 2000 | (JP) | 2000-117451 |

(51) Int. Cl.$^7$ .......................... C07D 471/02
(52) U.S. Cl. ................. 546/113; 546/14; 546/79; 546/18
(58) Field of Search .............. 546/113, 14, 18, 546/79

(56) References Cited

U.S. PATENT DOCUMENTS 5,057,406 A * 10/1991 Usagawa et al. ........... 430/522

FOREIGN PATENT DOCUMENTS

| EP | 1 106 621 A2 | 6/2001 |
| GB | 870753 A | 6/1961 |

OTHER PUBLICATIONS

Mikhailenko et al, Khimiya Geterotsiklicheskikh, Soedinenii (7), p. 948–951 (1982).*
Patent Abstracts of Japan—07-145148 (1995).
Patent Abstracts of Japan—05-287209 (1993).
XP-002231584—Abstract (1982).
XP-002231583—Abstract (1982).
European Search Report dated Mar. 5, 2003.

* cited by examiner

Primary Examiner—Bernard Dentz
(74) Attorney, Agent, or Firm—Sughrue Mion, PLLC

(57) ABSTRACT

There are provided fluorescent compounds that can be used for DNA sequencing, measurement of physiologically active substance or the like based on fluorescence immunoassay and so forth.

Compounds represented by the formula (I) ($V^1$ to $V^6$ represent a hydrogen atom or a functional group selected from the group consisting of a halogen atom, an alkyl group, an alkenyl group, a group that can form a covalent bond with a compound to be labeled and the like, and $V^1$, $V^2$ and others may bind to each other to form a saturated or unsaturated ring; $R^1$ represents a hydrogen atom or a functional group selected from the group consisting of an alkyl group, an aryl group and a heterocyclic group; $R^3$ and $R^4$ represent an alkyl group, and $R^3$ and $R^4$ may bind to each other to form a ring; Q represents a group of atoms required to form a methine dye chromophore; and m and n represent 0 or 1, provided that m+n is 1) or salts thereof General formula (I)

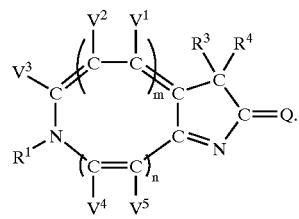

1 Claim, No Drawings

COMPOUNDS FOR FLUORESCENCE LABELING

This application is a 371 of PCT/JP00/0640, filed Sep. 20, 2000.

TECHNICAL FIELD

The present invention relates to highly sensitive fluorescence-labeling agents, which are used for DNA sequencing or measurement of physiologically active substance or the like based on fluorescence immunoassay, or used as a fluorescence contrast medium that is administered into a blood vessel to visualize information in vivo and the like. The invention also relates to synthetic intermediates for said agents.

BACKGROUND ART

For DNA sequencing and measurement of physiologically active substance or the like based on fluorescence immunoassay, methods have conventionally been used which comprise the step of labeling a target substance with a radioisotope. However, these methods have problems from viewpoints of safety, storability of agents or the like, and therefore, various methods for labeling a target substance with a fluorescent dye have been studied as alternatives to the above methods. Performances required for fluorescence-labeling agents include, for example, (1) agents should have a high fluorescence quantum yield, (2) should have a high molecular extinction coefficient, (3) should be water-soluble and should not aggregate in an aqueous solvent to cause self-quenching, (4) should be hardly hydrolyzed, (5) should hardly cause photodegradation, (6) should be hardly influenced by background fluorescence, and (7) should be introduced with a reactive substituent that produces a covalent bond with a target substance.

Fluorescein isothiocyanate (FITC) and rhodamine isothiocyanate, which have been known as fluorescence-labeling agents since old days, have a high fluorescence quantum yield. However, they have a low molecular extinction coefficient. In addition, they suffer from a problem that they are susceptible to background fluorescence of a membrane used for blotting since their excitation and emission wavelengths are within the range of 500 nm to 600 nm.

As dyes having a high molecular extinction coefficient, for example, cyanine dyes disclosed in U.S. Pat. No. 5,486,616, Japanese Patent Unexamined Publication (Kokai) Nos. 2-191674, 5-287209, 5-287266, 8-47400, 9-127115, 7-145148 and 6-222059, and polymethine dyes such as oxonol barbiturate disclosed in Journal of Fluorescence, 5, p.231 (1995) have been known. However, these dyes generally have a problem of a low fluorescence quantum yield. Further, these dyes also have a problem that they are hardly soluble in water and that they are hydrolyzed even if they are dissolved in water. In addition, they also suffer from a problem that they form aggregates in an aqueous medium due to their strong intermolecular interaction among dye molecules and thus self-quenching of fluorescence is often observed.

The cyanine dyes disclosed in Japanese Patent Unexamined Publication No. 2-191674 and other publications are superior dyes with water-solubility and suppressed formation of aggregates based on introduction of sulfonate group into a relatively stable chromophore. However, the dyes do not have satisfactorily high fluorescence quantum yield, and they suffers from a problem that synthesis of the dyes becomes difficult due to the introduction of sulfonate group.

Under the circumstances, development of fluorescent dyes has been desired which have high water-solubility and stability and are free from self-quenching of fluorescence due to aggregation, as well as characteristic of strong fluorescence.

As other dye backbone structure with strong fluorescence, azaindolenine cyanine dyes disclosed in British Patent No. 870,753 have been known. However, the patent publication is silent about characteristics essential for fluorescence-labeling agents such as water-solubility, aggregation property and stability of aqueous solutions. Furthermore, no example is given as to introduction of a reactive substituent that produces a covalent bond with a target substance. Therefore, their suitability as fluorescence-labeling agents remains completely unknown. Further, Japanese Patent Unexamined Publication Nos. 4-358143, 3-195668, 1-280750 and European Patent Laid-open EP841958 disclose applications of the azaindolenine cyanines for photographic purpose. However, the aforementioned applications utilize absorption characteristics of the azaindolenine cyanines, and do not consider and actively utilize their luminescence characteristics.

DISCLOSURE OF THE INVENTION

An object of the present invention is to provide a compound that is useful as a highly sensitive fluorescence-labeling agent used for DNA sequencing or measurement of physiologically active substances or the like based on fluorescence immunoassay, or used as a fluorescence contrast medium that is administered into a blood vessel to visualize information in vivo. Another object of the present invention is to provide a compound useful as synthetic intermediates for preparation of the aforementioned compounds. The inventors of the present invention conducted various studies to achieve the aforementioned objects, and as a result, they successfully achieved the aforementioned objects by providing the following compounds.

The present invention thus provides compounds represented by the following general formula (I) or salts thereof:

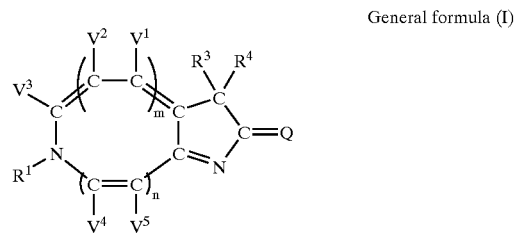

General formula (I)

wherein, $V^1$, $V^2$, $V^3$, $V^4$ and $V^5$ each independently represent a hydrogen atom or a group selected from the group consisting of a halogen atom, an alkyl group, an alkenyl group, an alkynyl group, an aryl group, a heterocyclic group, cyano group, a hydroxy group, nitro group, carboxyl group, an alkoxy group, an aryloxy group, a silyloxy group, a heterocyclyloxy group, an acyloxy group, a carbamoyloxy group, an alkoxycarbonyloxy group, an aryloxycarbonyloxy group, an amino group (including an anilino group), an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclylthio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, a carbamoyl group, a phosphono group, a phosphonato group and a group that can form a covalent bond with a compound to be labeled (each of said group may be substituted), provided that $V^1$, $V^2$, $V^3$, $V^4$ and $V^5$ do not simultaneously represent a hydrogen atom and provided that $V^1$ and $V^2$, $V^2$ and $V^3$, and $V^4$ and $V^5$ may independently bind to each other to form a saturated or unsaturated ring that may be substituted; $R^1$ represents a hydrogen atom or a group selected from the group consisting of an alkyl group, an aryl group and a heterocyclic group (each of said group may be substituted); $R^3$ and $R^4$ represent an alkyl group that may be substituted, and $R^3$ and $R^4$ may bind to each other to form a ring that may be substituted; Q represents a group of atoms required to form a cyanine dye chromophore, a melocyanine dye chromophore or a stilyl dye chromophore; and m and n represent 0 or 1, provided that m+n is 1.

The present invention also provides compounds represented by the following general formula (II):

General Formula (II)

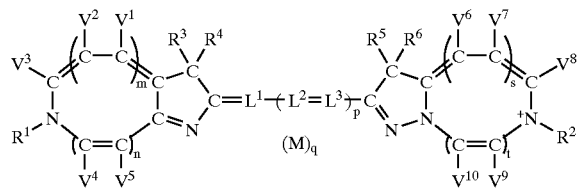

wherein, $V^1$, $V^2$, $V^3$, $V^4$, $V^5$, $V^6$, $V^7$, $V^8$, $V^9$ and $V^{10}$ each independently represent a hydrogen atom or a group selected from the group consisting of a halogen atom, an alkyl group, an alkenyl group, an alkynyl group, an aryl group, a heterocyclic group, cyano group, hydroxy group, nitro group, carboxyl group, an alkoxy group, an aryloxy group, a silyloxy group, a heterocyclyloxy group, an acyloxy group, a carbamoyloxy group, an alkoxycarbonyloxy group, an aryloxycarbonyloxy group, an amino group (including an anilino group), an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclylthio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, a carbamoyl group, a phosphono group, phosphonato group and a group that can form a covalent bond with a compound to be labeled (each of said group may be substituted), provided that $V^1$, $V^2$, $V^3$, $V^4$ and $V^5$ do not simultaneously represent a hydrogen atom, and provided that $V^1$ and $V^2$, $V^3$ and $V^3$, $V^4$ and $V^5$, $V^6$ and $V^7$, $V^7$ and $V^8$, and $V^9$ and $V^{10}$ may each independently form a saturated or unsaturated ring; $R^1$ and $R^2$ each independently represent a hydrogen atom or a group selected from the group consisting of an alkyl group, an aryl group and a heterocyclic group (each of said group may be substituted); $R^3$, $R^4$, $R^5$ and $R^6$ each independently represent an alkyl group that may be substituted, and $R^3$ and $R^4$, and $R^5$ and $R^6$ may bind to each other to independently form a ring that may be substituted; m, n, s and t represent 0 or 1, provided that m+n is 1 and s+t is 1; $L^1$, $L^2$ and $L^3$ each independently represent a methine group that may be substituted; p represents 1, 2 or 3; M represents a counter ion, and q represents a number required to neutralize the charge of the molecule.

The present invention further provides compounds represented by the following general formula (III) or salts thereof:

General Formula (III)

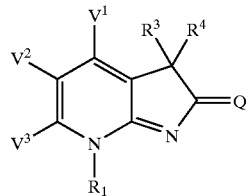

wherein, $V^1$, $V^2$ and $V^3$ each independently represents a hydrogen atom or a group selected from the group consisting of a halogen atom, an alkyl group, an alkenyl group, an alkynyl group, an aryl group, a heterocyclic group, cyano group, hydroxy group, nitro group, carboxyl group, an alkoxy group, an aryloxy group, a silyloxy group, a heterocyclyloxy group, an acyloxy group, a carbamoyloxy group, an alkoxycarbonyloxy group, an aryloxycarbonyloxy group, an amino group (including an anilino group), an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclylthio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, a carbamoyl group, a phosphono group, a phosphonato group and a group that can form a covalent bond with a labeling compound (each of said group may be substituted), provided that $V^1$, $V^2$ and $V^3$ do not simultaneously represent a hydrogen atom, and provided that $V^1$ and $V^2$, and $V^2$ and $V^3$ may each independently form a saturated or unsaturated ring that may be substituted; $R^1$ represents a hydrogen atom or a group selected from the group consisting of an alkyl group, an aryl group and a heterocyclic group (each of said group may be substituted); $R^3$ and $R^4$ each independently represent an alkyl group that may be substituted, and $R^3$ and $R^4$ may bind to each other to form a ring that may be substituted; and compounds represented by the following general formula (IV):

General Formula (IV)

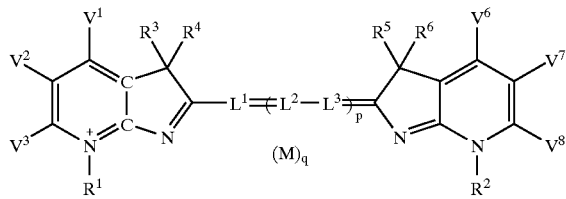

wherein, $V^1$, $V^2$, $V^3$, $V^6$, $V^7$ and $V^8$ represent a hydrogen atom or a group selected from the group consisting of a halogen atom, an alkyl group, an alkenyl group, an alkynyl group, an aryl group, a heterocyclic group, cyano group, hydroxy group, nitro group, carboxyl group, an alkoxy group, an aryloxy group, a silyloxy group, a heterocyclyloxy group, an acyloxy group, a carbamoyloxy group, an alkoxycarbonyloxy group, an aryloxycarbonyloxy group, an amino group (including an anilino group), an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclylthio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, a carbamoyl group, a phosphono group, a phosphonato group and a group that can form a covalent bond with a compound to be labeled (each of said group may be substituted), provided that $V^1$, $V^2$ and $V^3$ do not simultaneously represent a hydrogen atom, and provided that $V^1$ and $V^2$, $V^2$ and $V^3$, $V^6$ and $V^7$, and $V^7$ and $V^8$ may each independently form a saturated or unsaturated ring that may be substituted; $R^1$ and $R^2$ each independently represent a hydrogen atom or a group selected from the group consisting of an alkyl group, an aryl group and a heterocyclic group (each of said group may be substituted); $R^3$, $R^4$, $R^5$ and $R^6$ each independently represent an alkyl group that may be substituted, and $R^3$ and $R^4$, and $R^5$ and $R^6$ may each independently bind to each other to form a ring that may be substituted; $L^1$, $L^2$ and $L^3$ each independently represent a methine group that may be substituted; p represents 1, 2 or 3; M represents a counter ion; and q represents a number required to neutralize the charge of the molecule.

According to preferred embodiments of the present invention, provided are:

the compounds represented by the general formula (III) or (IV), wherein at least one of $V^1$, $V^2$ and $V^3$ is a group selected from the group consisting of a halogen atom, an alkenyl group, an alkynyl group, an aryl group, a heterocyclic group, cyano group, an alkylthio group, an arylthio group, a heterocyclylthio group, an alkylsulfonyl group, and an arylsulfonyl group;

the compounds wherein at least one of $V^1$, $V^2$ and $V^3$ is a group selected from the group consisting of a halogen atom, an alkynyl group, an aryl group and a heterocyclic group;

the compounds represented by the general formula (III) or (IV), wherein at least one of $V^1$, $V^2$ and $V^3$ is an aryl group substituted with a sulfo group or a salt thereof, a heterocyclic group substituted with a sulfo group or a salt thereof, or an alkynyl group substituted with a sulfo group or a salt thereof; and the compounds represented by the general formula (III) or (IV), wherein at least one of $R^1$ and $R^2$ is an alkyl group or aryl group substituted with a reactive substituent that can form a covalent bond, inonic bond or coordinate bond with a substance to be labeled.

According to more preferred embodiments of the present invention, provided are the compounds represented by the general formula (III) or (IV) or the aforementioned preferred compounds, wherein at least one of $R^1$ and $R^2$ is an alkyl group or aryl group substituted with a group that can form a covalent bond with an amino group, hydroxyl group or thiol group of a substance to be labeled; or wherein at least one of $R^1$ and $R^2$ is an alkyl group substituted with a carboxyl group.

The present invention also provides compounds represented by the following general formula (V):

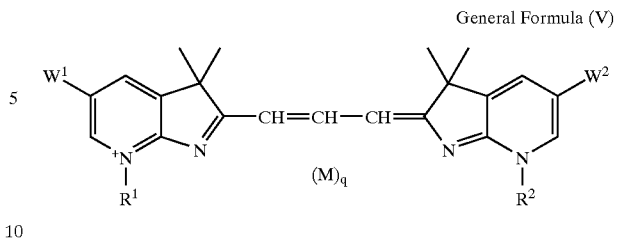

General Formula (V)

wherein, $R^1$ and $R^2$ each independently represent a hydrogen atom, or an alkyl group, an aryl group, or a heterocyclic group (each of said group may be substituted), provided that at least one of $R^1$ and $R^2$ is an alkyl group or aryl group substituted with a reactive substituent that can form a covalent bond, inonic bond, or coordinate bond with a substance to be labeled; M represents a counter ion; q represents a number required to neutralize the charge of the molecule; and $W^1$ and $W^2$ each independently represent a hydrogen atom or a group selected from the group consisting of a halogen atom, an alkynyl group, an aryl group, a heterocyclic group, an alkylthio group, and an arylthio group, provided that $W^1$ and $W^2$ do not simultaneously represent a hydrogen atom.

The present invention further provides compounds represented by the following general formula (VI):

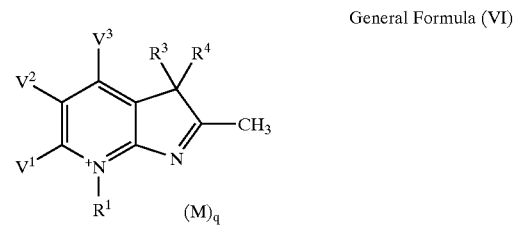

General Formula (VI)

wherein, $V^1$, $V^2$ and $V^3$ each independently represent a hydrogen atom or a group selected from the group consisting of a halogen atom, an alkyl group, an alkenyl group, an alkynyl group, an aryl group, a heterocyclic group, cyano group, hydroxy group, nitro group, carboxyl group, an alkoxy group, an aryloxy group, a silyloxy group, a heterocyclyloxy group, an acyloxy group, a carbamoyloxy group, an alkoxycarbonyloxy group, an aryloxycarbonyloxy group, an amino group (including an anilino group), an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclylthio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, a carbamoyl group, a phosphono group, a phosphonato group and a group that can form a covalent bond with a compound to be labeled (each of said group may be substituted), provided that $V^1$, $V^2$ and $V^3$ do not simultaneously represent a hydrogen atom, and $V^1$ and $V^2$, and $V^2$ and $V^3$ may each independently form a saturated or unsaturated ring that may be substituted; $R^1$ represents a hydrogen atom or a group selected from the group consisting of an alkyl group, an aryl group and a heterocyclic group (each of said group may be substituted); $R^3$ and $R^4$ represent an alkyl group that may be substituted, and $R^3$ and $R^4$ may bind to each other to form a ring that may be substituted, and compounds represented by the following general formula (VII) or salts thereof:

General Formula (VII)

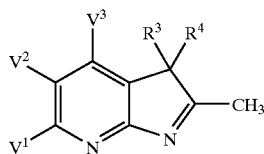

wherein, $V^1$, $V^2$ and $V^3$ each independently represent a hydrogen atom or a group selected from the group consisting of a halogen atom, an alkyl group, an alkenyl group, an alkynyl group, an aryl group, a heterocyclic group, cyano group, hydroxy group, nitro group, carboxyl group, an alkoxy group, an aryloxy group, a silyloxy group, a heterocyclyloxy group, an acyloxy group, a carbamoyloxy group, an alkoxycarbonyloxy group, an aryloxycarbonyloxy group, an amino group (including an anilino group), an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclylthio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, a carbamoyl group, a phosphono group, a phosphonato group, and a group that can form a covalent bond with a compound to be labeled (each of said group may be substituted), provided that $V^1$, $V^2$ and $V^3$ do not simultaneously represent a hydrogen atom, and provided that $V^1$ and $V^2$, and $V^2$ and $V^3$ may each independently form a saturated or unsaturated ring that may be substituted; $R^1$ represents a hydrogen atom or a group selected from the group consisting of an alkyl group, an aryl group and a heterocyclic group (each of said group may be substituted); $R^5$ and $R^6$ represent an alkyl group that may be substituted, and $R^5$ and $R^6$ may bind to each other to form a ring that may be substituted.

From other aspects of the present invention, provided are a fluorescence-labeling agent comprising the aforementioned compound; a substance fluorescence-labeled with the aforementioned compound, preferably a substance for diagnosis labeled with the aforementioned compound; an agent for diagnosis comprising a diagnostic substance fluorescence-labeled with the aforementioned compound; a method for diagnosis comprising a use of a diagnostic substance fluorescence-labeled with the aforementioned compound; a use of the aforementioned compound for manufacture of the aforementioned agent for diagnosis; a fluorescence contrast medium for administration into a blood vessel to visualize information in vivo, which comprises the aforementioned compound; and a use of the aforementioned compound for manufacture of the aforementioned fluorescence contrast medium.

BEST MODE FOR CARRYING OUT THE INVENTION

In the present specification, an alkyl group may have any of straight, branched and cyclic chain or a combination thereof, and examples thereof include a straight or branched alkyl group having 1 to about 30 carbon atoms such as methyl group, ethyl group, n-propyl group, isopropyl group, t-butyl group, n-octyl group, eicosyl group, and 2-ethylhexyl group; a substituted or unsubstituted cycloalkyl group or an alkyl consisting of a combination of a cycloalkyl group and a straight or branched alkyl group, which has 3 to 30 carbon atoms, for example, cyclohexyl group, cyclopentyl group, and 4-n-dodecylcyclohexyl group; a bicycloalkyl group having 5 to 30 carbon atoms such as bicyclo[1,2,2]heptan-2-yl group and bicyclo[2,2,2]octan-3-yl group; a tricycloalkyl group and the like. The same shall apply to an alkyl moiety of a substituent having the alkyl moiety (e.g., alkylthio group and the like). Further, examples of substituted alkyl groups include, for example, 2-chloroethyl, 2-cyanoethyl and the like. A halogen atom referred to in the specification may be any of fluorine atom, chlorine atom, bromine atom, and an iodine atom. When a functional group or a ring structure is referred to as "may be substituted" (or as "substituted or unsubstituted") in the present specification, the description means that the functional group or ring may have one or more substituents. However, types, numbers, and substituting positions of the substituents are not particularly limited.

As $V^1$, $V^2$, $V^3$, $V^4$ and $V^5$ in the general formula (I), a hydrogen atom or a functional group may be used which is selected from the group consisting of a halogen atom, an alkyl group, an alkenyl group, an alkynyl group, an aryl group, a heterocyclic group, cyano group, hydroxy group, nitro group, carboxyl group, an alkoxy group, an aryloxy group, a silyloxy group, a heterocyclyloxy group, an acyloxy group, a carbamoyloxy group, an alkoxycarbonyloxy group, an aryloxycarbonyloxy group, an amino group (including an anilino group), an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclylthio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, a carbamoyl group, a phosphono group, a phosphonato group, and a group that can form a covalent bond with a compound to be labeled. These groups may have one or more substituents at any positions, and when they have two or more substituents, the substituents may be the same or different. $V^1$, $V^2$, $V^3$, $V^4$ and $V^5$ do not simultaneously represent a hydrogen atom.

Specific examples of the aforementioned groups, including those having one or more substituents, are a halogen atom (e.g., chlorine atom, bromine atom, iodine atom and the like), an alkyl group (those exemplified above or the like), an alkenyl group [straight, branched, or cyclic alkenyl groups and those consisting of a combination thereof can be used, and examples include a straight or branched alkenyl group having 2 to 30 carbon atoms such as vinyl group, allyl group, prenyl group, geranyl group, and oleyl group; a cycloalkenyl group having 3 to 30 carbon atoms such as 2-cyclopenten-1-yl group and 2-cyclohexen-1-yl group; a bicycloalkenyl group having 5 to 30 carbon atoms such as bicyclo[2,2,1]hept-2-en-1-yl group and bicyclo[2,2,2]oct-2-en-4-yl group], an alkynyl group (preferably a substituted or unsubstituted alkynyl group having 2 to 30 carbon atoms such as ethynyl group, propargyl group, trimethylsilylethynyl group, phenylethynyl group, p-sulfophenylethynyl group, p-sulfonylaminophenylethynyl group and m-sulfonylaminophenylethynyl group), an aryl group (preferably a substituted or unsubstituted aryl group having 6 to 30 carbon atoms such as phenyl group, p-tolyl group, naphthyl group, m-chlorophenyl group, and o-hexadecanoylaminophenyl group), a heterocyclic group (said group corresponds to a monovalent residue obtained by removing one hydrogen atom from an aromatic or non-aromatic heterocyclic compound, which is preferably a 5- or 6-membered substituted or unsubstituted heterocyclic group, further preferably a 5- or 6-membered aromatic heterocyclic group having 3 to 30 carbon atoms, such as 2-furyl group, 2-thienyl group, 2-pyrimidinyl group, and 2-benzothiazolyl group), cyano group, hydroxyl group, nitro group, carboxyl group, an alkoxy group (preferably a substituted or unsubstituted alkoxy group having 1 to 30 carbon atoms such as methoxy group, ethoxy group, isopropoxy group, t-butoxy group, n-octyloxy group and 2-methoxyethoxy group), an aryloxy group (preferably a substituted or unsubstituted aryloxy group having 6 to 30 carbon atoms such as phenoxy group, 2-methylphenoxy group, 4-t-butylphenoxy group, 3-nitrophenoxy group, and 2-tetradecanoylaminophenoxy group), a silyloxy group (preferably a silyloxy group having 3 to 20 carbon atoms such as trimethylsilyloxy group and t-butyldimethylsilyloxy group), a heterocyclyloxy group (preferably a substituted or unsubstituted heterocyclyloxy group having 2 to 30 carbon atoms such as 1-phenyltetrazole-5-oxy group and 2-tetrahydropyranyloxy group), an acyloxy group (preferably formyloxy group, a substituted or unsubstituted alkylcarbonyloxy group having 2 to 30 carbon atoms or a substituted or unsubstituted arylcarbonyloxy group having 6 to 30 carbon atoms, for example, formyloxy group, acetyloxy group, pivaloyloxy group, stearoyloxy group, benzoyloxy group, p-methoxyphenylcarbonyloxy group and the like), a carbamoyloxy group (preferably a substituted or unsubstituted carbamoyloxy group having 1 to 30 carbon atoms such as N,N-dimethylcarbamoyloxy group, N,N-diethylcarbamoyloxy group, morpholinocarbonyloxy group, N,N-di-n-octylaminocarbonyloxy group and N-n-octylcarbamoyloxy group), an alkoxycarbonyloxy group (preferably a substituted or unsubstituted alkoxycarbonyloxy group having 2 to 30 carbon atoms such as methoxycarbonyloxy group, ethoxycarbonyloxy group, t-butoxycarbonyloxy group, and n-octylcarbonyloxy group), an aryloxycarbonyloxy group (preferably a substituted or unsubstituted aryloxycarbonyloxy group having 7 to 30 carbon atoms such as phenoxycarbonyloxy group, p-methoxyphenoxycarbonyloxy group and p-n-hexadecyloxyphenoxycarbonyloxy group), an amino group (preferably an amino group, a substituted or unsubstituted alkylamino group having 1 to 30 carbon atoms, and a substituted or unsubstituted anilino group having 6 to 30 carbon atoms, for example, amino group, methylamino group, dimethylamino group, anilino group, N-methylanilino group, diphenylamino group and the like), an acylamino group (preferably formylamino group, a substituted or unsubstituted alkylcarbonylamino group having 1 to 30 carbon atoms or a substituted or unsubstituted arylcarbonylamino group having 6 to 30 carbon atoms, for example, formylamino group, acetylamino group, pivaloylamino group, lauroylamino group, benzoylamino group, 3,4,5-tri-n-octyloxyphenylcarbonylamino group and the like), an aminocarbonylamino group (preferably a substituted or unsubstituted aminocarbonylamino group having 1 to 30 carbon atoms such as carbamoylamino group, N,N-dimethylaminocarbonylamino group, N,N-diethylaminocarbonylamino group and morpholinocarbonylamino group), an alkoxycarbonylamino group (preferably a substituted or unsubstituted alkoxycarbonylamino group having 2 to 30 carbon atoms such as methoxycarbonylamino group, ethoxycarbonylamino group, t-butoxycarbonylamino group, n-octadecyloxycarbonylamino group and N-methylmethoxycarbonylamino group), an aryloxycarbonylamino group (preferably a substituted or unsubstituted aryloxycarbonylamino group having 7 to 30 carbon atoms such as phenoxycarbonylamino group, p-chlorophenoxycarbonylamino group and m-n-octyloxyphenoxycarbonylamino group), a sulfamoylamino groups (preferably a substituted or unsubstituted sulfamoylamino group having 0 to 30 carbon atoms such as sulfamoylamino group, N,N-dimethylaminosulfonylamino group and N-n-octylaminosulfonylamino group), an alkylsulfonyl group or an arylsulfonylamino group (preferably a substituted or unsubstituted alkylsulfonylamino group having 1 to 30 carbon atoms or a substituted or unsubstituted arylsulfonylamino group having 6 to 30 carbon atoms, for example, methylsulfonylamino group, butylsulfonylamino group, phenylsulfonylamino group, 2,3,5-trichlorophenylsulfonylamino group, p-methylphenylsulfonylamino group and the like), a mercapto group, an alkylthio group (preferably a substituted or unsubstituted alkylthio group having 1 to 30 carbon atoms such as methylthio group, ethylthio group and n-hexadecylthio group), an arylthio group (preferably a substituted or unsubstituted arylthio group having 6 to 30 carbon atoms such as phenylthio group, p-chlorophenylthio group and m-methoxyphenylthio group), a heterocyclylthio group (preferably a substituted or unsubstituted heterocyclylthio group having 2 to 30 carbon atoms such as 2-benzothiazolylthio group and 1-phenyltetrazol-5-ylthio group), a sulfamoyl group (preferably a substituted or unsubstituted sulfamoyl group having 0 to 30 carbon atoms such as N-ethylsulfamoyl group, N-(3-dodecyloxypropyl) sulfamoyl group, N,N-dimethylsulfamoyl group, N-acetylsulfamoyl group, N-benzoylsulfamoyl group and N-(N'-phenylcarbamoyl)sulfamoyl group), an alkylsulfinyl group or an arylsulfinyl group (preferably a substituted or unsubstituted alkylsulfinyl group having 1 to 30 carbon atoms or a substituted or unsubstituted arylsulfinyl group having 6 to 30 carbon atoms, for example, methylsulfinyl group, ethylsulfinyl group, phenylsulfinyl group and p-methylphenylsulfinyl group), an alkylsulfonyl group or an arylsulfonyl group (preferably a substituted or unsubstituted alkylsulfonyl group having 1 to 30 carbon atoms or a substituted or unsubstituted arylsulfonyl group having 6 to 30 carbon atoms, for example, methylsulfonyl group, ethylsulfonyl group, phenylsulfonyl group, p-methylphenylsulfonyl group and the like), an acyl group (preferably formyl group, a substituted or unsubstituted alkylcarbonyl group having 2 to 30 carbon atoms or a substituted or unsubstituted arylcarbonyl group having 7 to 30 carbon atoms, for example, acetyl group, pivaloyl group, 2-chloroacetyl group, stearoyl group, benzoyl group, p-n-octyloxyphenylcarbonyl group and the like), an aryloxycarbonyl group (preferably a substituted or unsubstituted aryloxycarbonyl group having 7 to 30 carbon atoms such as phenoxycarbonyl group, o-chlorophenoxycarbonyl group, m-nitrophenoxycarbonyl group and p-t-butylphenoxycarbonyl group), an alkoxycarbonyl group (preferably a substituted or unsubstituted alkoxycarbonyl group having 2 to 30 carbon atoms such as methoxycarbonyl group, ethoxycarbonyl group, t-butoxycarbonyl group and n-octadecyloxycarbonyl group), a carbamoyl group (preferably a substituted or unsubstituted carbamoyl group having 1 to 30 carbon atoms such as carbamoyl group, N-methylcarbamoyl group, N,N-dimethylcarbamoyl group, N,N-di-n-octylcarbamoyl group and N-(methylsulfonyl) carbamoyl group), a phosphono group, a phosphonato group, and a group that can form a covalent bond with a substance to be labeled (e.g., an isothiocyanato group an isocyanato group, a succinimidyl ester group, a halogen-substituted triazinyl group, a halogen-substituted pyrimidinyl group, a sulfonyl halide group, an α-haloacetyl group, a maleimidyl group, an aziridinyl group and the like).

When the aforementioned functional groups is substituted, the aforementioned groups or sulfonic acid group or a salt thereof can be used as the substituent. Examples of the substituent on the aforementioned functional groups include a sulfonic acid group or a salt thereof, as well as an alkylcarbonylaminosulfonyl group, an arylcarbonylaminosulfonyl group, an alkylsulfonylaminocarbonyl group, an arylsulfonylaminocarbonyl group and the like. More specifically, examples of substituents on the aforementioned functional groups include a sulfonic acid group or a salt thereof, methylsulfonylaminocarbonyl group, p-methylphenylsulfonylaminocarbonyl group, acetylaminosulfonyl group, benzoylaminosulfonyl group and the like, and a sulfonic acid group or a salt thereof is preferred as the substituent.

$V^1$ and $V^2$, $V^2$ and $V^3$, and $V^4$ and $V^5$ may bind to each other to form a saturated or unsaturated ring. As the ring thus formed, a 5-, 6- or 7-membered ring is preferred. Further, the ring may contain one or more hetero atoms (a hetero atom referred to in the specification means, for example, an oxygen atom, a nitrogen atom, a sulfur atom, a metal atom or the like), and when two or more hetero atoms are contained, they may be the same or different. Further, one or more substituents such as those explained as for $V^1$ and others may exist at any position on the ring formed, and when two or more substituents exist, they may be the same or different.

Preferred as $V^1$, $V^2$, $V^3$, $V^4$ and $V^5$ are a halogen atom, an alkyl group having 1 to 6 carbon atoms, an alkenyl group having 2 to 30 carbon atoms, an alkynyl group having 2 to 30 carbon atoms, an aryl group having 6 to 20 carbon atoms, a heterocyclic group (a 5- or 6-membered aromatic or non-aromatic substituted or unsubstituted heterocyclic group, preferably a 5- or 6-membered aromatic heterocyclic having 3 to 30 carbon atoms), an alkylthio group having 1 to 30 carbon atoms, an arylthio group having 6 to 30 carbon atoms, a substituted or unsubstituted heterocyclylthio group having 2 to 30 carbon atoms, a sulfamoyl group having 0 to 30 carbon atoms, an alkylsulfonyl group having 1 to 30 carbon atoms and an arylsulfonyl group having 6 to 30 carbon atoms. An isothiocyanato group, an isocyanato group, a succinimidyl ester group, a halogen-substituted triazinyl group, a halogen-substituted pyrimidinyl group, a sulfonyl halide group, an α-haloacetyl group, a maleimidyl group and an aziridinyl group, which can form a covalent bond with a substance to be labeled, are also preferred.

Further preferred as $V^1$, $V^2$, $V^3$, $V^4$ and $V^5$ are a halogen atom, an alkyl group having 1 to 6 carbon atoms, an alkynyl group having 2 to 30 carbon atoms, an aryl group having 6 to 20 carbon atoms, a heterocyclic group, an alkylthio group having 1 to 30 carbon atoms, an arylthio group having 6 to 30 carbon atoms, a substituted or unsubstituted heterocyclylthio group having 2 to 30 carbon atoms, and the group that can form a covalent bond with a substance to be labeled, which is explained above.

As $R^1$ in the general formula (I), for example, a hydrogen atom, an alkyl group having 1 to 20 carbon atoms (e.g., methyl group, ethyl group, propyl group, butyl group, cyclohexyl group and the like), an aryl group having 6 to 20 carbon atoms (e.g., phenyl group, tolyl group, naphthyl group and the like) and a heterocyclic group (e.g., 2-pyridyl group, 4-pyridyl group, pyrazolyl group, triazolyl group, tetrazolyl group and the like) can be used. The aforementioned alkyl group, aryl group, and heterocyclic group may have one or more substituents at any positions. Types of the substituents are not particularly limited, and the groups explained as for the aforementioned $V^1$ or others and a sulfonic acid group or a salt thereof, as well as a reactive substituent for labeling a substance to be labeled through a covalent bond, an ionic bond, a hydrogen bond or the like may exist.

Examples of the substance to be labeled include antibody, protein, peptide, enzyme substrate, hormone, lymphokine, metabolic product, receptor, antigen, hapten, lectin, avidin, streptavidin, toxin, carbohydrate, polysaccharide, nucleic acid, deoxynucleic acid, nucleic acid derivatives, deoxynucleic acid derivatives, DNA fragment, RNA fragment, DNA fragment derivatives, RNA fragment derivatives, naturally-derived drug, virus particle, bacterium particle, virus component, yeast component, blood cell, blood cell component, bacterium, bacterial component, natural or synthetic lipid, drug, poison, environmental pollutant, polymer, polymer particle, glass particle, plastic particle, polymer membrane and the like. Examples of the reactive substituent for labeling these substances through a covalent bond, ionic bond or hydrogen bond include, for example, a succinimidyl ester group, a halogen-substituted triazinyl group, a halogen-substituted pyrimidinyl group, a sulfonyl halide group, an α-haloacetyl group, a maleimidyl group, an aziridinyl group and the like.

$R^1$ is preferably a substituted or unsubstituted alkyl group having 1 to 20 carbon atoms, more preferably a substituted alkyl group having 1 to 20 carbon atoms. Examples of preferred substituents on the alkyl group include the aforementioned reactive substituents, as well as carboxyl group, an amino group, hydroxy group, a mercapto group, a sulfonic acid group or a salt thereof, an alkylamido group (an alkyl moiety of said alkylamido group may have one or more substituents selected from the group consisting of the aforementioned reactive substituents, carboxyl group, an amino group, hydroxy group and a mercapto group) and the like.

In the general formula (I), Q represents a group of atoms required to form a methine dye chromophore. Types of the methine dye are not particularly limited. Preferred methine dyes include, for example, cyanine dyes, merocyanine dyes, rhodacyanine dyes, trinucleous merocyanine dyes, tetranucleous merocyanine dyes, allopolar dyes, styryl dyes, styryl base dyes, hemicyanine dyes, streptocyanine dyes, hemioxonole dyes and the like, more preferred dyes include cyanine dyes, merocyanine dyes and rhodacyanine dyes, and most preferred dyes include cyanine dyes (as for their charged state, they may be in any form of cation, anion, or betaine). Details of these dyes are described in F. M. Harmer, "Heterocyclic Compounds—Cyanine Dyes and Related Compounds", John Wiley and Sons, New York, London, 1964; D. M. Sturmer, "Heterocyclic Compounds—Special Topics in Heterocyclic Chemistry", Chapter 18, Section 14, 482 to 515 pages, John Wiley and Sons, New York, London, 1977 and the like.

As the cyanine dyes, merocyanine dyes, and rhodacyanine dyes, those disclosed in U.S. Pat. No. 5,340,694, pages 21 and 22, (XI), (XII) and (XIII) are preferred. More preferred are those represented by the general formula (I) of the present invention wherein cyanine dye structure of the formula (II) is formed.

In the general formula (II), $V^1$, $V^2$, $V^3$, $V^4$, $V^5$, $V^6$, $V^7$, $V^8$, $V^9$ and $V^{10}$ have the same meanings as $V^1$ mentioned in the general formula (I). $V^1$ to $V^{10}$ are independent from one another, however, $V^1$, $V^2$, $V^3$, $V^4$ and $V^5$ do not simultaneously represent a hydrogen atom. $R^1$ and $R^2$ are independent from each other, and they have the same meaning as $R^1$ mentioned in the general formula (I). $R^3$, $R^4$, $R^5$ and $R^6$ are independent from one another, and they have the same meaning as $R^3$ and $R^4$ mentioned in the general formula (I).

In the general formula (II), $L^1$, $L^2$ and $L^3$ represent a substituted or unsubstituted methine group. Examples of the substituents existing on the methine group include a substituted or unsubstituted alkyl group having 1 to 15 carbon atoms, preferably 1 to 10 carbon atoms, most preferably 1 to 5 carbon atoms (e.g., methyl group, ethyl group, carboxyethyl group and the like), a substituted or unsubstituted aryl group having 6 to 30 carbon atoms, preferably 6 to 20 carbon atoms, most preferably 6 to 15 carbon atoms (e.g., phenyl group, o-carboxyphenyl group and the like), a substituted or unsubstituted heterocyclic group having 3 to 20 carbon atoms, preferably 4 to 15 carbon atoms, most preferably 6 to 10 carbon atoms (e.g., N,N-dimethylbarbituric acid group and the like), a halogen atom (e.g., fluorine atom, chlorine atom, bromine atom, iodine atom and the like), an alkoxy group having 1 to 20 carbon atoms, preferably 1 to 15 carbon atoms, most preferably 1 to 10 carbon atoms (e.g., methoxy group, ethoxy group and the like), an amino group having 0 to 20 carbon atoms, preferably 2 to 15 carbon atoms, most preferably 4 to 15 carbon atoms (e.g., methylamino group, dimethylamino group, N-methyl-N-phenylamino group, N-methylpiperazino group and the like), an alkylthio group having 1 to 15 carbon atoms, preferably 1 to 10 carbon atoms, most preferably 1 to 8 carbon atoms (e.g., methylthio group, ethylthio group and the like), an arylthio groups having 6 to 20 carbon atoms, preferably 6 to 18 carbon atoms, most preferably 6 to 15 carbon atoms (e.g., phenylthio group, p-methylthio group and the like).

When the compounds of the present invention are used for diagnostic purpose, it is preferred that the aforementioned substituents are further substituted with a reactive group such as a succinimidyl ester group, a halogen-substituted triazinyl group, a halogen-substituted pyrimidinyl group, a sulfonyl halide group, an α-haloacetyl group, a maleimidyl group and an aziridinyl group. Symbol "p" represents 1, 2 or 3. Symbol "p" is preferably 1 or 2, and p is most preferably 1 which corresponds to the structure represented by the general formula (V).

M represents a counter ion. M may be a cation or an anion, and examples of the cation include an alkali metal ion such as sodium ion, potassium ion and lithium ion and an organic ion such as tetraalkylammonium ion and pyridinium ion. The anion may be an inorganic anion or an organic anion. Examples of the anion include a halogen anion (e.g., fluorine ion, chlorine ion, bromine ion, iodine ion), a substituted arylsulfonate ion (e.g., p-toluenesulfonate ion, p-chlorobenzenesulfonate ion), an aryldisulfonate ion (e.g., 1,3-benzenedisulfonate ion, 1,5-naphthalenedisulfonate ion), an alkylsulfate ion (e.g., methylsulfate ion), sulfate ion, thiocyanate ion, perchlorate ion, tetrafluoroborate ion, picrate ion, acetate ion, trifluoromethanesulfonate ion and the like. M may be a hydrogen ion. Preferred counter ions are an ammonium ion, an alkali metal ion, a halogen anion and a substituted arylsulfonate ion, and more preferred are an alkali metal ion, a halogen anion and a substituted arylsulfonate ion. Symbol "q" represents a number required to neutralize charge of the molecule.

In the general formula (III), $V^1$, $V^2$, $V^3$, $R^1$, $R^3$, $R^4$ and Q have the same meanings as those of the general formula (I), respectively. In the general formula (IV), $V^1$, $V^2$, $V^3$, $V^6$, $V^7$, $V^8$, $R^1$, $R^2$, $R^3$, $R^4$, $R^5$, $R^6$, $L^1$, $L^2$, $L^3$, M, p and q have the same meanings as those of the general formula (II), respectively. In the general formula (VI), $V^1$, $V^2$, $V^3$, $R^1$, $R^3$, $R^4$, M and q have the same meanings as those of the general formula (II), respectively. In the general formula (VII), $V^1$, $V^2$, $V^3$, $R^3$, and $R^4$ have the same meanings as those of the general formula (II), respectively.

In the general formula (V), $R^1$, $R^2$, M and q have the same meanings as those of the general formula (II), respectively. The halogen atom, alkynyl group, aryl group, heterocyclic group, alkylthio group and arylthio group represented by $W^1$ and $W^2$ have the same meanings as the groups explained as for $V^1$ and others in the formula (I), respectively. It is preferred that at least one acid group (e.g., a sulfonic acid group or a salt thereof, carboxylic acid group, phosphoric acid group and the like) is introduced on each of the aforementioned substituents except for the halogen. The acid group may bind to the aforementioned alkynyl group, aryl group, heterocyclic group, alkylthio group or arylthio group via a bridging group such as an alkylene group, however, it is preferred that the acid group directly binds to the aforementioned substituents.

The compounds of the present invention may exist as acid addition salts, and they may exist as base addition salts depending on types of substituents. Examples of the salts include mineral acid salts such as hydrochloride, sulfate, nitrate and phosphate, organic acid salts such as methanesulfonate, p-toluenesulfonate, tartrate, citrate and maleate, metal salts such as sodium salt, potassium salt and calcium salt, ammonium salts, organic amine salts such as triethylamine salt, amino acid salts such as and glycine salt and the like. Further, the compounds of the present invention may exist as hydrates or solvates, and each of these substances also falls within the scope of the present invention. Further, the compounds of the present invention may have one or more asymmetric carbons depending on types of the substituents, and any of stereoisomers such as optical isomers and diastereoisomers, mixtures of stereoisomers, racemates and the like also falls within the scope of the present invention.

Preferred examples of the compounds of the present invention represented by the aforementioned general formulas are shown below. However, the scope of the present invention is not limited to the following specific compounds.

| No. | V¹ | V⁷ | R¹ | R² | M |
|---|---|---|---|---|---|
| I-11 | 4-ethynyl-phenyl-N(SO₂CH₃)(CH₂)₃SO₃⁻ | 4-ethynyl-phenyl-N(SO₂CH₃)(CH₂)₃SO₃⁻ | -CH(SO₃⁻)(CH₂CH₃)(CH₂CH₂CH₃) | -(CH₂)₅-COOH | 2K⁺ |
| I-12 | 3-ethynyl-5-(H₃CO₂S)-phenyl-N((CH₂)₃SO₃⁻) | 3-ethynyl-5-(H₃CO₂S)-phenyl-N((CH₂)₃SO₃⁻) | -(CH₂)₃SO₃⁻ | -(CH₂)₅-COOH | 2K⁺ |
| I-13 | 4-ethynyl-phenyl-N(SO₂CH₃)(CH₂)₅COOH | 4-ethynyl-phenyl-N(SO₂CH₃)(CH₂)₃SO₃⁻ | -CH(SO₃⁻)(CH₂CH₃)(CH₂CH₂CH₃) | -SO₃⁻ (butyl) | 2K⁺ |
| I-14 | 3-ethynyl-5-(H₃CO₂S)-phenyl-N((CH₂)₃SO₃⁻) | 3-ethynyl-5-(H₃CO₂S)-phenyl-N((CH₂)₃SO₃⁻) | -(CH₂)₃SO₃⁻ (butyl) | -(CH₂)₃SO₃⁻ (butyl) | 2K⁺ |
| I-15 | 3-ethynyl-5-(H₃CO₂S)-phenyl-N((CH₂)₃SO₃⁻) | 3-ethynyl-5-(H₃CO₂S)-phenyl-N((CH₂)₅COOH) | -NH-C(O)-CH₂CH₃ (2,5-disulfonatophenyl) | -NH-C(O)-CH₂CH₃ (2,5-disulfonatophenyl) | 4Na⁺ |

-continued

| No. | V¹ | V⁷ | R¹ | R² | M |
|---|---|---|---|---|---|
| I-16 | HC≡C-CH₂-OH | HC≡C-CH₂-OH | -CH₂-CH(OH)-CH₂-SO₃⁻ | -(CH₂)₅-COOH | — |
| I-17 | HC≡C-CH₂-OSO₃⁻ | HC≡C-CH₂-OSO₃⁻ | -CH₂-CH(OSO₃⁻)-CH₂-SO₃⁻ | -(CH₂)₅-COOH | 3K⁺ |
| I-18 | HC≡C-C(CH₃)₂-OH | HC≡C-C(CH₃)₂-OH | -CH₂-CH(OH)-CH₂-SO₃⁻ | -(CH₂)₅-CONH-(CH₂)₂COOH | — |
| I-19 | HC≡C-C(CH₃)₂-OH | HC≡C-C(CH₃)₂-OH | 2-methyl-4,5-disulfonatophenyl | -(CH₂)₅-COOH | K⁺ |
| I-20 | HC≡C-C(CH₃)₂-OH | HC≡C-C(CH₃)₂-OH | -CH₂CONH-(2-NH, 4-SO₃⁻ phenyl with 1-SO₃⁻) | -(CH₂)₅-COOH | K⁺ |

-continued

General structure: bis-indolenine trimethine cyanine dye with V¹, V⁷ substituents on the rings, R¹ and R² on the ring nitrogens, and M counterion.

| No. | V¹ | V⁷ | R¹ | R² | M |
|---|---|---|---|---|---|
| I-21 | —C≡C—CH₂—OSO₃⁻ | —C₆H₄—C≡CH (4-SO₃⁻) | —CH₂—CH(Et)—CH(OSO₃⁻)—CH₂SO₃⁻ | —(CH₂)₅—COO—N-succinimidyl | 3K⁺ |
| I-22 | 2-methylbenzofuran-5-yl | 2-methylbenzofuran-5-yl | —CH(CH₃)CH₂CH₂CH₃ (with SO₃⁻) | —(CH₂)₅—COOH | — |
| I-23 | 2-methylbenzofuran-5-yl | 4-(O(CH₂)₃SO₃⁻)-phenyl-methyl | —(CH₂)₄SO₃⁻ | —(CH₂)₅—COOH | K⁺ |
| I-24 | 2-methylbenzofuran-5-yl | H | —(CH₂)₄SO₃⁻ | —(CH₂)₅—COOH | — |
| I-25 | 2-methylfuran-5-yl | 2-methylfuran-5-yl | 3,5-disulfonato-methylphenyl | —(CH₂)₅—CONH—(4,6-dichloro-1,3,5-triazin-2-yl) | Na⁺ |

-continued

[Structure: cyanine dye with two 3,3-dimethyl-pyrrolo-pyridinium units connected by a trimethine bridge, bearing substituents V¹, V⁷, R¹, R² and counterion M]

| No. | V¹ | V⁷ | R¹ | R² | M |
|---|---|---|---|---|---|
| I-26 | 2-thienyl | 2-thienyl | 4-$SO_3^-$-2-methylphenyl (with $O_3S$ and methyl) | —(CH$_2$)$_5$—NHCO(CH$_2$)$_5$SS-(2-pyridyl) | Na$^+$ |
| I-27 | 4-O(CH$_2$)$_3$SO$_3^-$-phenyl | 4-O(CH$_2$)$_3$SO$_3^-$-phenyl | sec-pentyl-SO$_3^-$ | —(CH$_2$)$_5$—COOH | 2K$^+$ |
| I-28 | 2-methyl-5-SO$_3^-$-phenyl | 2-methyl-5-SO$_3^-$-phenyl | n-butyl-SO$_3^-$ | —(CH$_2$)$_5$—COOH | 2K$^+$ |
| I-29 | 3,5-di(SO$_3^-$)-phenyl | 3,5-di(SO$_3^-$)-phenyl | n-butyl-SO$_3^-$ | —(CH$_2$)$_5$—COOH | 4K$^+$ |
| I-30 | phenyl | phenyl | —(CH$_2$)$_4$—N$^+$(CH$_3$)$_3$ | —(CH$_2$)$_4$—N$^+$(CH$_3$)$_3$ | 2I$^-$ |

| No. | V | R¹ | R² | M |
|---|---|---|---|---|
| I-31 | —CF₃ | —CH₃ | —(CH₂)₅—COO⁻ | — |
| I-32 | —CN | CH₃CH₂CH₂CH(CH₃)—SO₃⁻ (pentan-2-yl sulfonate) | —(CH₂)₅—COOH | — |
| I-33 | —OH | —(CH₂)₃—SO₃⁻ | —(CH₂)₅—COO—N(succinimidyl) | — |
| I-34 | —NO₂ | —(CH₂)₃—SO₃⁻ | —(CH₂)₅—COO—N(succinimidyl) | — |
| I-35 | —COOH | —(CH₂)₃—SO₃⁻ | —(CH₂)₅—NCS | — |
| I-36 | —OCH₃ | —CH₂CONH—(2,5-disulfonatophenyl) | —(CH₂)₅—CONH—(4,6-dichloro-1,3,5-triazin-2-yl) | K⁺ |
| I-37 | —O—C₆H₅ | CH₃CH₂CH₂CH(CH₃)—SO₃⁻ | —(CH₂)₅—COOH | — |
| I-38 | —OSi(CH₃)₃ | —CH₃ | —(CH₂)₅—COO⁻ | — |
| I-39 | —O—(pyrimidin-2-yl) | —CH₃ | —(CH₂)₅—CONH—(4,6-dihydroxy-1,3,5-triazin-2-yl) | I⁻ |
| I-40 | —OCOCH₃ | —CH₃ | —(CH₂)₅—N(piperazinyl)N—(CH₂)₅COO⁻ | — |
| I-41 | —OCONH₂ | —CH₃ | —(CH₂)₅—COO⁻ | — |
| I-42 | —OCOOCH₃ | —(CH₂)₃—SO₃⁻ | —(CH₂)₅—COOH | — |

-continued

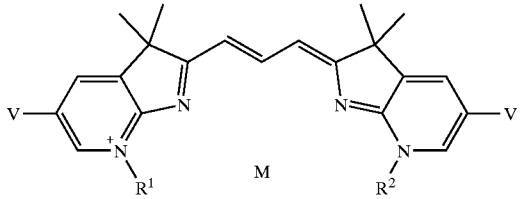

| | V | R¹ | R² | |
|---|---|---|---|---|
| I-43 | 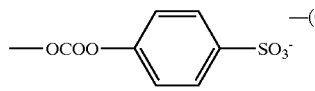 —OCOO—C₆H₄—SO₃⁻ | —(CH$_2$)$_3$—SO$_3^-$ | —(CH$_2$)$_5$—NCS | 2Na⁺ |
| I-44 | —N(CH$_3$)$_2$ | —(CH$_2$)$_3$—SO$_3^-$ | —(CH$_2$)$_5$—NCS | — |
| I-45 | —NHCO(CH$_2$)COOH | —(CH$_2$)$_3$—SO$_3^-$ | —(CH$_2$)$_5$—SO$_3^-$ | K⁺ |
| I-46 | —NHCONH$_2$ | 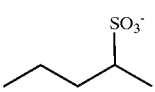 sec-butyl-SO$_3^-$ | —(CH$_2$)$_5$—COOH | — |
| I-47 | —NHCOOCH$_3$ | —CH$_3$ | —(CH$_2$)$_5$—COO⁻ | — |
| I-48 | —NHSO$_2$NH$_2$ | —CH$_3$ | —(CH$_2$)$_5$—COO⁻ | — |
| I-49 | —NHSO$_2$CH$_3$ | 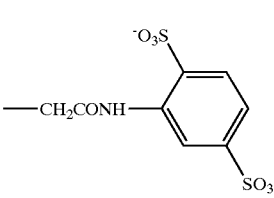 —CH$_2$CONH—C$_6$H$_3$(SO$_3^-$)$_2$ | —(CH$_2$)$_5$—NCS | K⁺ |
| I-50 | 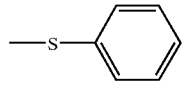 —S—C$_6$H$_5$ | 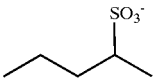 sec-butyl-SO$_3^-$ | 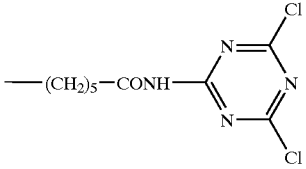 —(CH$_2$)$_5$—CONH-(4,6-dichloro-1,3,5-triazin-2-yl) | — |
| I-51 | 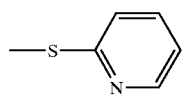 —S-(2-pyridyl) | —CH$_3$ | —(CH$_2$)$_5$—COO⁻ | — |
| I-52 | —SO$_2$NH$_2$ | —(CH$_2$)$_3$—SO$_3^-$ | —(CH$_2$)$_5$—COOH | — |
| I-53 | —SOCH$_3$ | —(CH$_2$)$_3$—SO$_3^-$ | —(CH$_2$)$_5$—COOH | — |
| I-54 | —SO$_2$CH$_3$ | —(CH$_2$)$_3$—SO$_3^-$ | —(CH$_2$)$_5$—COOH | — |
| I-55 | —COCH$_3$ | —CH$_3$ | —(CH$_2$)$_5$—COO⁻ | — |
| I-56 | —COOC$_2$H$_5$ | —CH$_3$ | —(CH$_2$)$_5$—COO⁻ | — |
| I-57 | 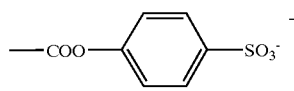 —COO—C$_6$H$_4$—SO$_3^-$ | —CH$_3$ | —(CH$_2$)$_5$—COO⁻ | 2K⁺ |
| I-58 | —CONH(CH$_2$)$_2$COOH | —CH$_3$ | —(CH$_2$)$_5$—COO⁻ | — |
| I-59 | —PO$_3^{--}$ | —(CH$_2$)$_3$—SO$_3^-$ | —(CH$_2$)$_5$—COOH | 4Na⁺ |

-continued
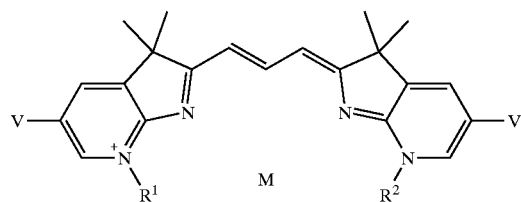
I-60
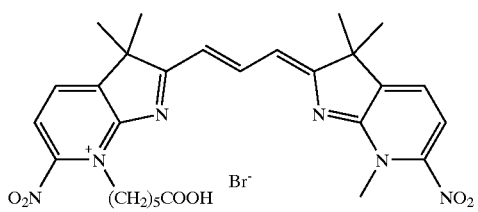
I-61
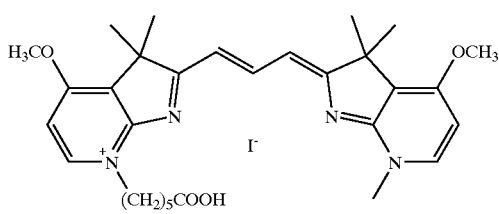
I-62
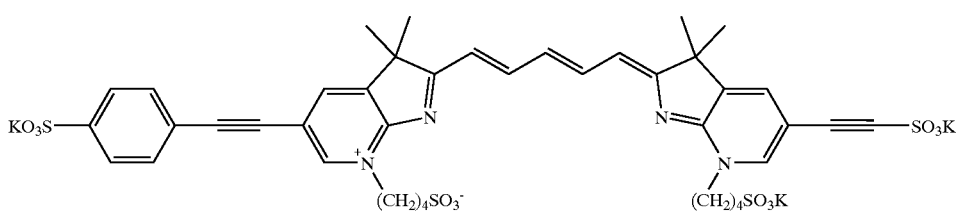
I-63
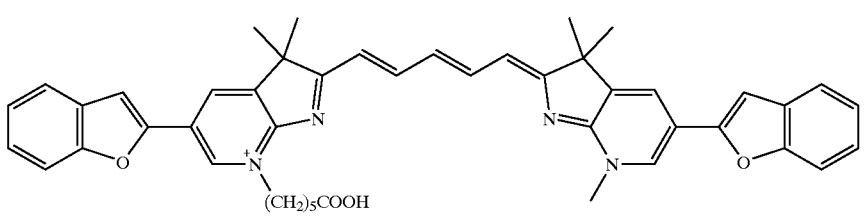
I-64
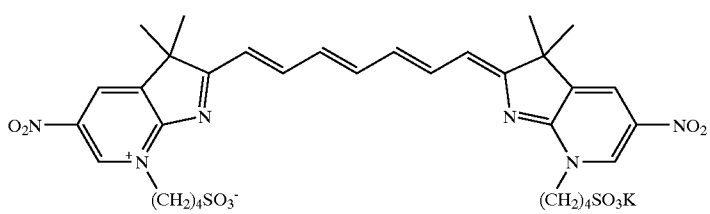
I-65
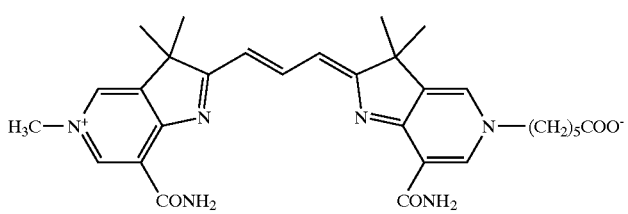

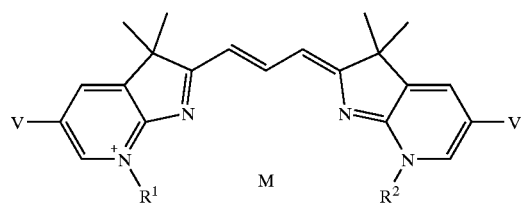
I-66 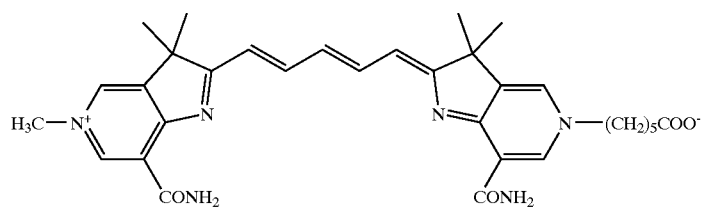
I-67 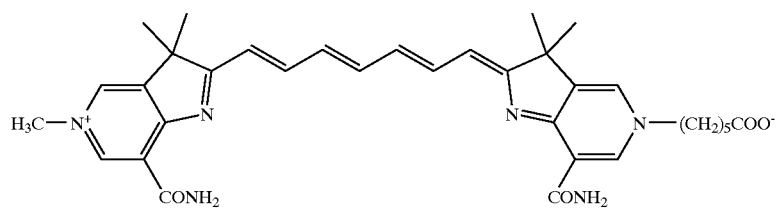
I-68 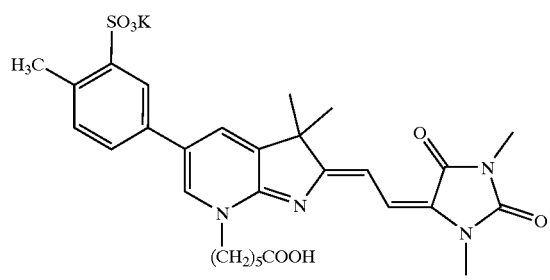
I-69 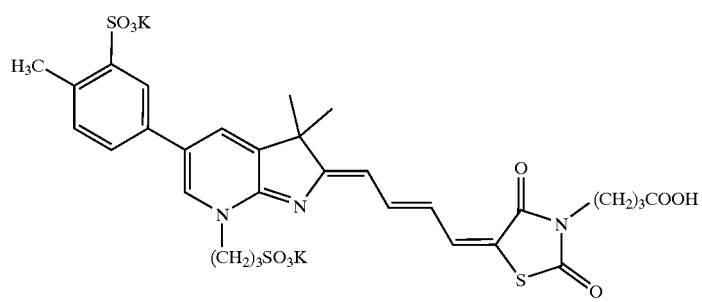
I-70 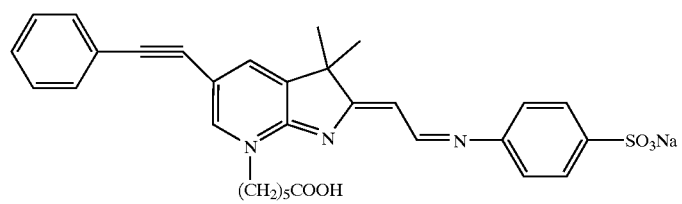

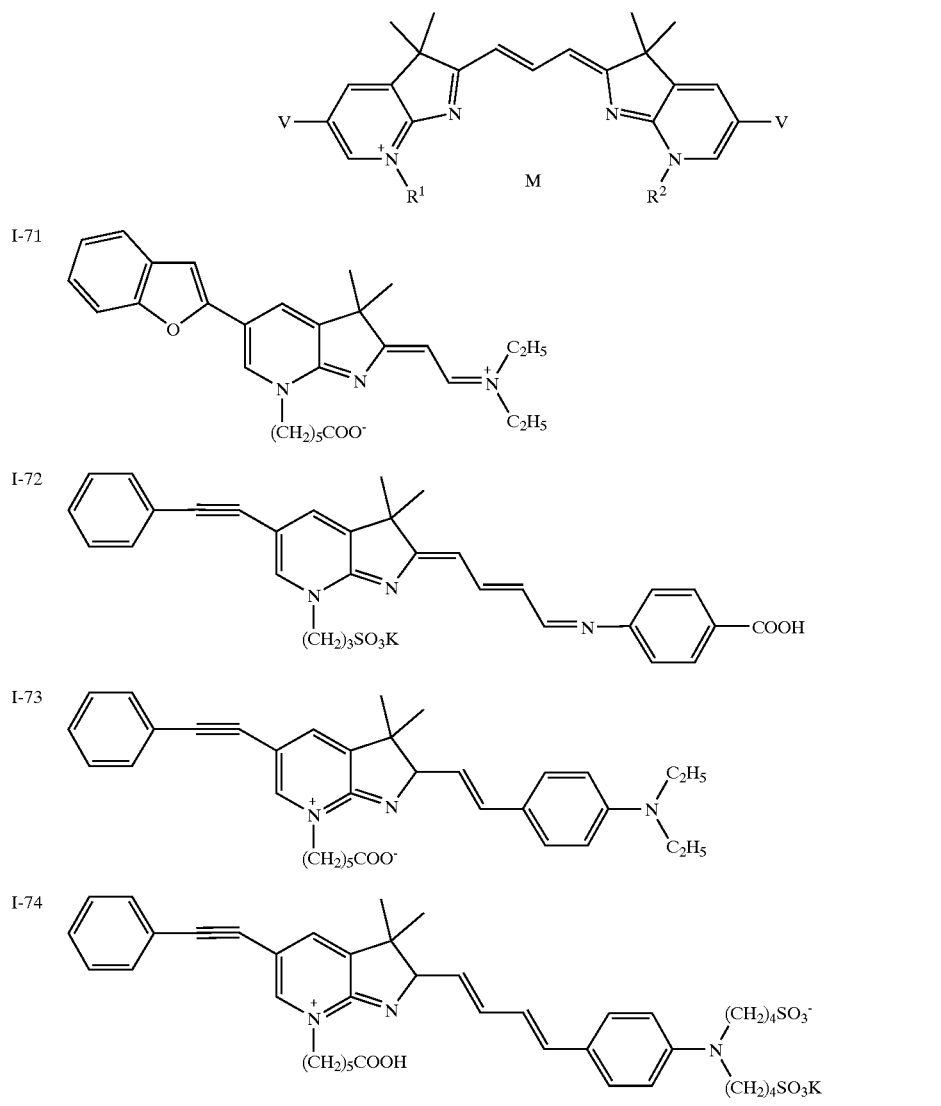
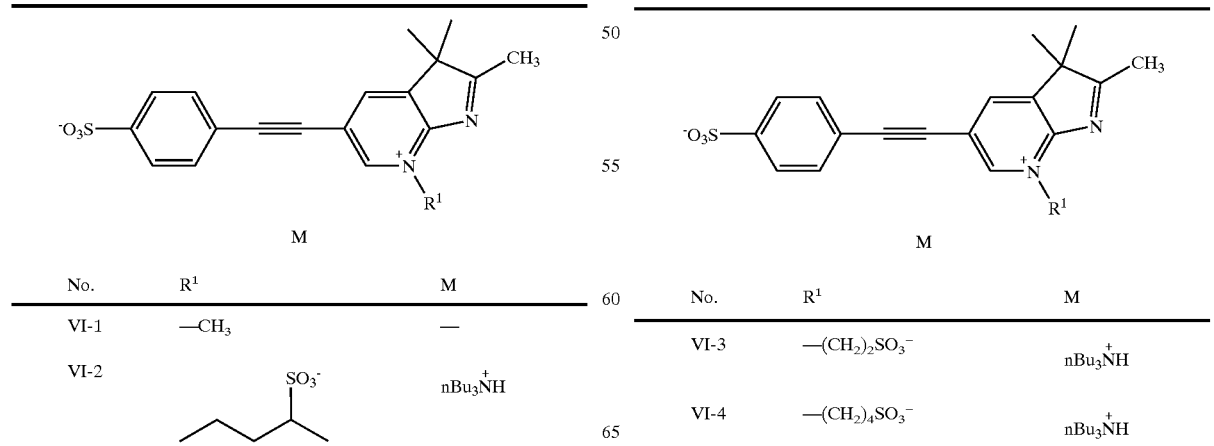

-continued
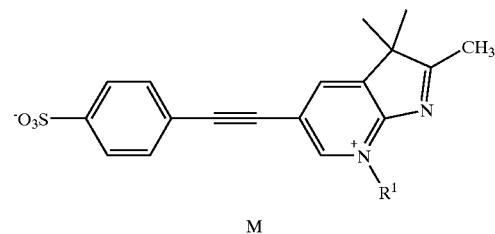
M
| No. | R¹ | M |
|---|---|---|
| VI-5 | | nBu₃NH⁺ |
| VI-6 | | nBu₃NH⁺ |
| VI-7 | —(CH₂)₅—COOC₂H₅ | — |
| VI-8 | —(CH₂)₁₁—COOCH₃ | — |
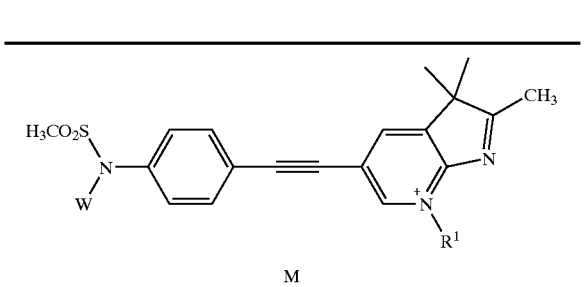
M
| No. | R¹ | W | M |
|---|---|---|---|
| VI-9 | | H | — |
| VI-10 | —(CH₂)₂SO₃⁻ | H | — |
| VI-11 | | H | Na⁺ |
| VI-12 | —(CH₂)₅—COOC₂H₅ | H | Br⁻ |
| VI-13 | | —(CH₂)₅—COOC₂H₅ | — |
| VI-14 | —(CH₂)₂SO₃⁻ | —(CH₂)₅—COOC₂H₅ | — |
-continued
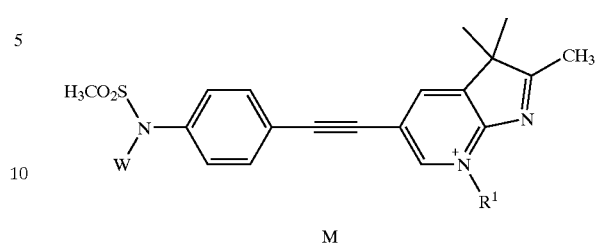
M
| No. | R¹ | W | M |
|---|---|---|---|
| VI-15 | | —(CH₂)₅—COOC₂H₅ | Na⁺ |
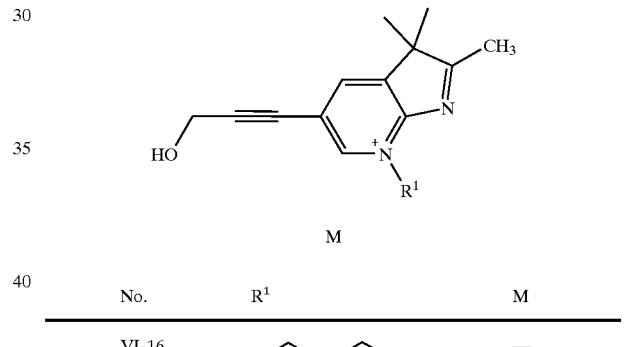
M
| No. | R¹ | M |
|---|---|---|
| VI-16 | | — |
| VI-17 | —(CH₂)₅COOC₂H₅ | Br⁻ |
M
| No. | R¹ | M |
|---|---|---|
| VI-18 | | — |

-continued

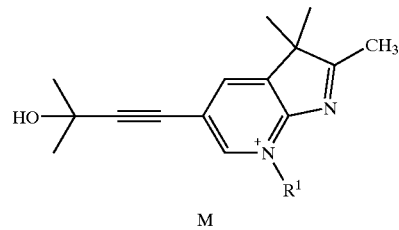
M

| No. | R¹ | M |
|---|---|---|
| VI-19 | 2-methyl-benzenedisulfonate | K⁺ |
| VI-20 | propionamido-benzenedisulfonate | Na⁺ |
| VI-21 | —(CH₂)₅COOC₂H₅ | Br⁻ |

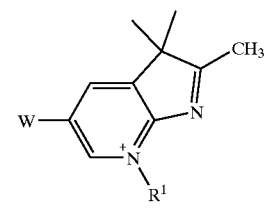
M

| No. | W | R¹ | M |
|---|---|---|---|
| VI-22 | 2-benzofuranyl | sec-pentylsulfonate | — |
| VI-23 | 2-benzofuranyl | —(CH₂)₅COOC₂H₅ | Br⁻ |
| VI-24 | 4-(O(CH₂)₃SO₃⁻)phenyl | sec-pentylsulfonate | Na⁺ |
| VI-25 | 4-(O(CH₂)₃SO₃⁻)phenyl | —(CH₂)₅COOC₂H₅ | — |

-continued

| No. | W | R¹ | M |
|---|---|---|---|
| VI-26 | 2-furyl | benzenedisulfonate (meta) | Na⁺ |
| VI-27 | 2-thienyl | 2-methyl-benzenedisulfonate | Na⁺ |
| VI-28 | 4-methylphenyl | —(CH₂)₃SO₃⁻ | — |

| No. | R¹ | W | M |
|---|---|---|---|
| VI-29 | sec-pentylsulfonate | H | — |
| VI-30 | —(CH₂)₂SO₃⁻ | H | — |
| VI-31 | propionamido-benzenedisulfonate | H | Na⁺ |
| VI-32 | —(CH₂)₅—COOC₂H₅ | H | Br⁻ |

-continued

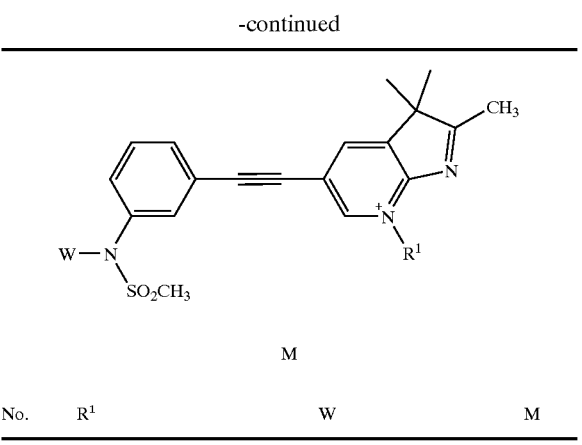

M

| No. | R¹ | W | M |
|---|---|---|---|
| VI-33 | ![sec-butyl SO₃⁻] | —(CH$_2$)$_5$—COOC$_2$H$_5$ | — |
| VI-34 | —(CH$_2$)$_2$SO$_3^-$ | —(CH$_2$)$_5$—COOC$_2$H$_5$ | — |
| VI-35 | ![propionamido benzene disulfonate] | —(CH$_2$)$_5$—COOC$_2$H$_5$ | Na⁺ |

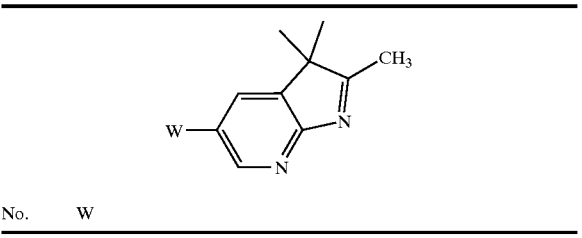

| No. | W |
|---|---|
| VII-1 | ![4-sulfophenyl ethynyl, nBu$_3$N] |
| VII-2 | ![4-(methanesulfonamido)phenyl ethynyl] |
| VII-3 | ![4-(N-methanesulfonyl-N-(CH$_2$)$_5$COOC$_2$H$_5$)phenyl ethynyl] |
| VII-4 | ![3-(methanesulfonamido)phenyl ethynyl] |

-continued

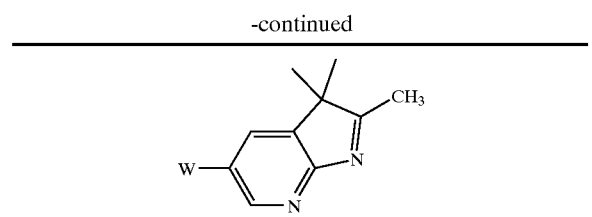

| No. | W |
|---|---|
| VII-5 | ![3-(N-methanesulfonyl-N-(CH$_2$)$_5$COOC$_2$H$_5$)phenyl ethynyl] |
| VII-6 | ![HOCH$_2$C≡C—] |
| VII-7 | ![(CH$_3$)$_2$C(OH)C≡C—] |
| VII-8 | ![2-benzofuryl] |
| VII-9 | ![2-furyl] |
| VII-10 | ![2-thienyl] |
| VII-11 | ![4-(O(CH$_2$)$_3$SO$_3$Na)phenyl] |
| VII-12 | ![4-methylphenyl] |
| VII-13 | —CF$_3$ |
| VII-14 | —CN |
| VII-15 | —OH |
| VII-16 | —NO$_2$ |
| VII-17 | —COOH |
| VII-18 | —OCH$_3$ |
| VII-19 | ![—O-phenyl] |
| VII-20 | ![—O—Si(CH$_3$)$_3$] |
| VII-21 | ![—O-2-pyrimidinyl] |
| VII-22 | —OCOCH$_3$ |
| VII-23 | —COCNH$_2$ |

-continued
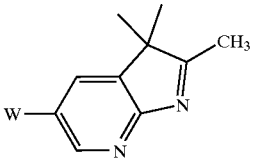
| No. | W |
|---|---|
| VII-24 | —OCOOCH₃ |
| VII-25 |  |
| VII-26 | —N(CH₃)₂ |
| VII-27 | —NHCO(CH₂)COOH |
| VII-28 | —NHCONH₂ |
| VII-29 | —NHCOOCH₃ |
| VII-30 | —NHSO₂NH₂ |
| VII-31 | —NHSO₂CH₃ |
| VII-32 |  |
| VII-33 |  |
| VII-34 | —SO₂NH₂ |
| VII-35 | —SOCH₃ |
| VII-36 | —SO₂CH₃ |
| VII-37 | —COCH₃ |
| VII-38 | —COOC₂H₅ |
| VII-39 |  |
| VII-40 | —CONH(CH₂)₂COOH |
| VII-41 | —PO⁼ |
| VII-42 | —Cl |
| VII-43 | —Br |
| VII-44 | 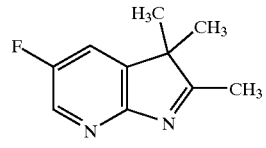 |
| VII-45 | 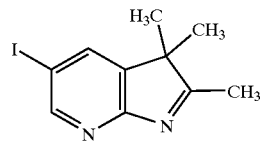 |
| VII-46 | 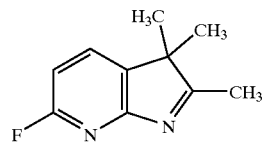 |
-continued
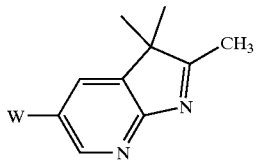
| No. | W |
|---|---|
| VII-47 | 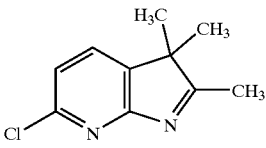 |
| VII-48 | 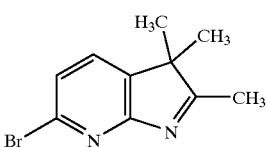 |
| VII-49 | 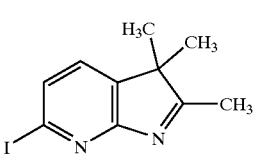 |
| VII-50 | 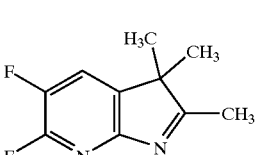 |
| VII-51 | 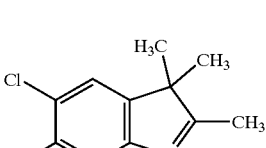 |
| VII-52 | 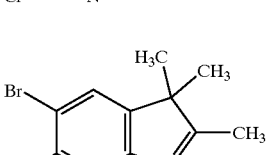 |
| VII-53 | 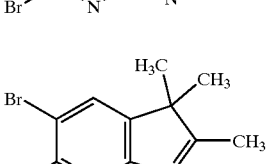 |
| VII-54 | 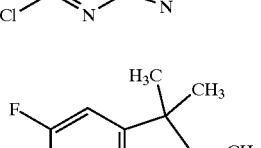 |

-continued
| No. | W |
|---|---|
| VII-55 | 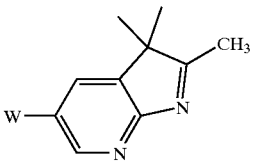 |
| VII-56 | 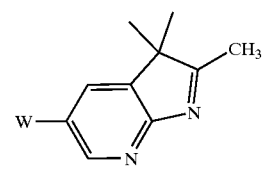 |
| VII-57 | 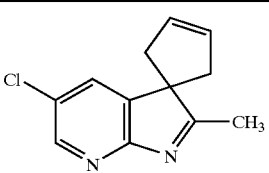 |
| VII-58 | 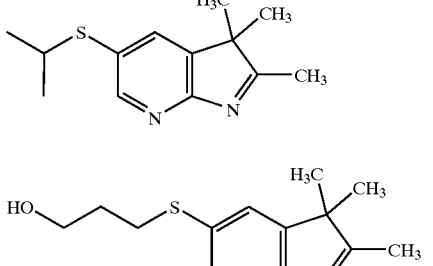 |
| VII-59 | 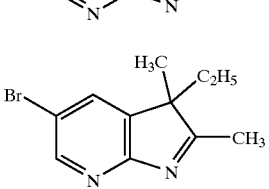 |
| VII-60 | 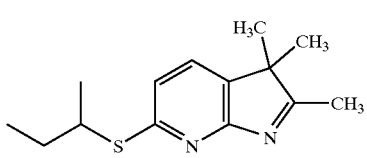 |
| VII-61 | 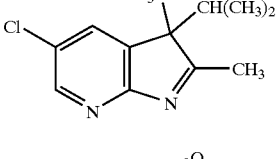 |
| VII-62 | 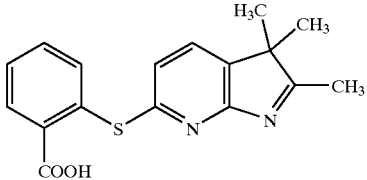 |
-continued
| No. | W |
|---|---|
| VII-63 | 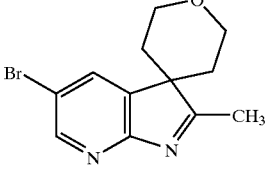 |
| VII-64 | 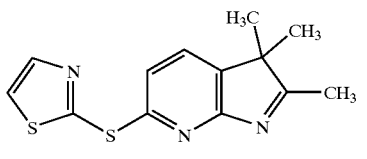 |
| VII-65 | 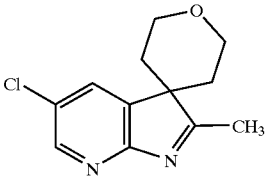 |
| VII-66 | 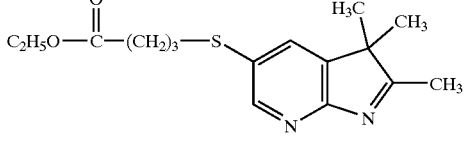 |
| VII-67 | 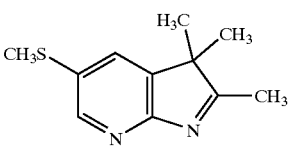 |
| VII-68 | 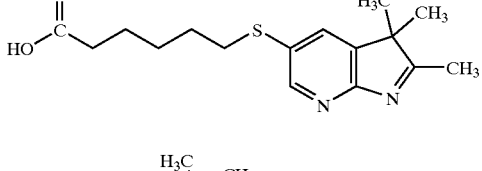 |
| VII-69 | 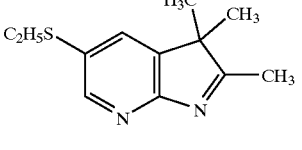 |
| VII-70 | 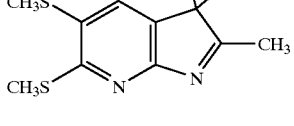 |

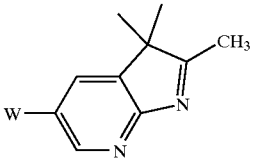
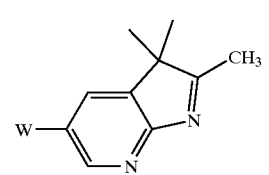

-continued
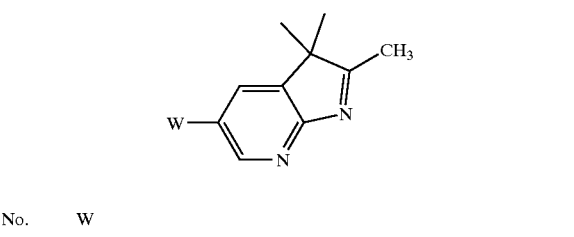
| No. | W |
|---|---|
| VII-86 | 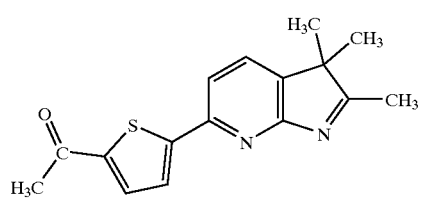 |
| VII-87 | 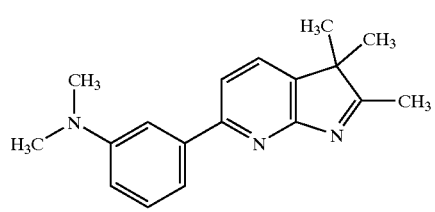 |
| VII-88 | 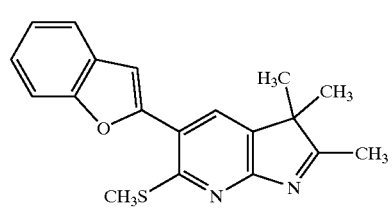 |
| VII-89 | 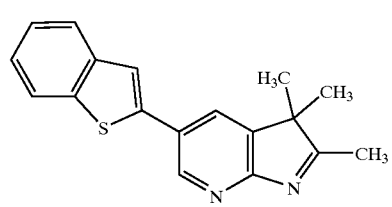 |
| VII-90 | 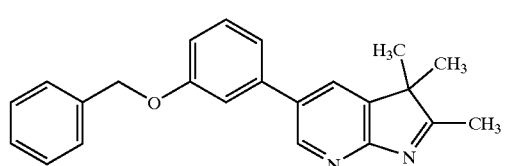 |
| VII-91 | 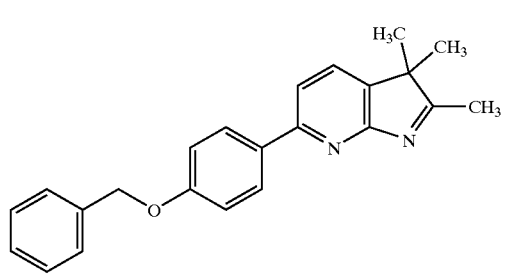 |
-continued
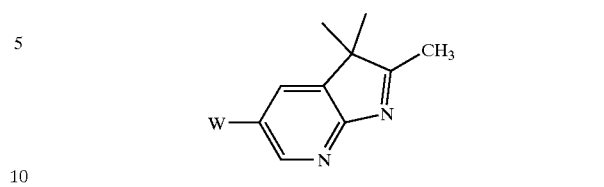
| No. | W |
|---|---|
| VII-92 | 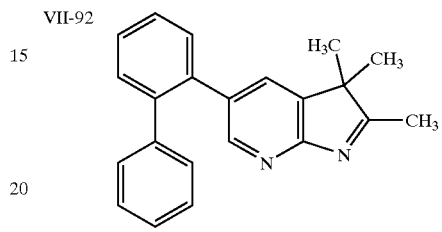 |
| VII-93 | 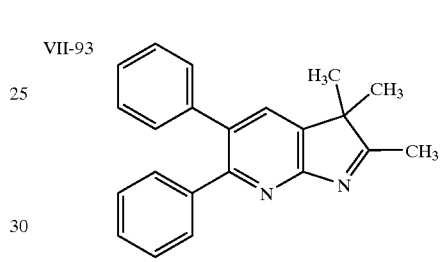 |
| VII-94 | 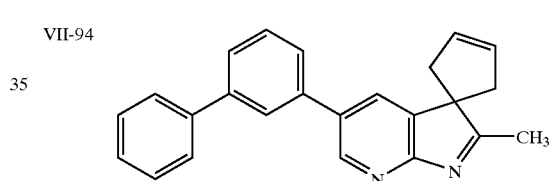 |
| VII-95 | 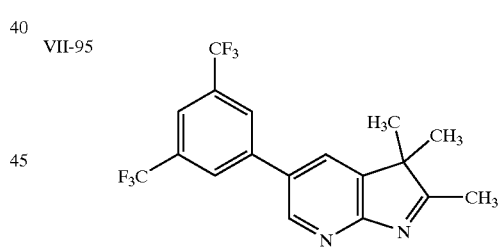 |
| VII-96 | $C_4H_9$ 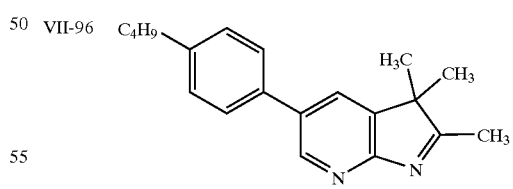 |
| VII-97 | 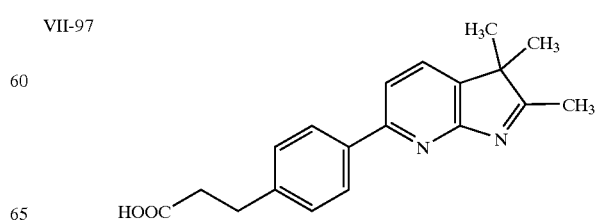 |

-continued

| No. | W |
|---|---|
| VII-98 | 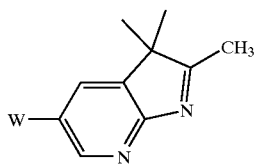 |
| VII-99 | 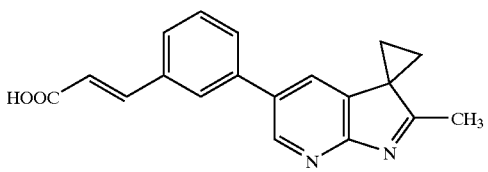 |
| VII-100 | 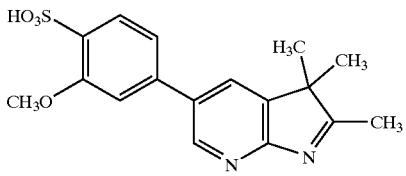 |
| VII-101 | 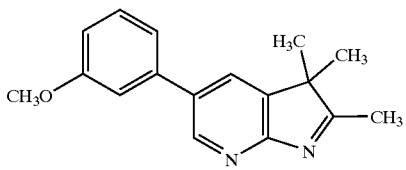 |
| VII-102 | 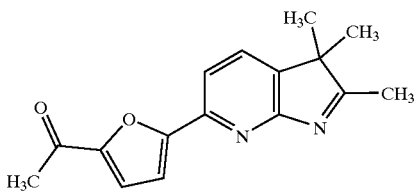 |
|  | 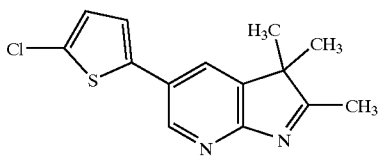 |

The compounds of the present invention represented by the aforementioned general formulas are useful as fluorescence-labeling agents. Substances that can be labeled with the compounds of the present invention are not particularly limited, and any substances can be used as an object of the labeling, which include low molecular compounds, high molecular compounds, organic compounds, inorganic compounds, biological substances, natural organic compounds, microorganisms and the like. More specifically, examples of the substances to be labeled include antibody, protein, peptide, enzyme substrate, hormone, lymphokine, metabolic product, receptor, antigen, hapten, lectin, avidin, streptavidin, toxin, carbohydrate, polysaccharide, nucleic acid, deoxynucleic acid, nucleic acid derivative, deoxynucleic acid derivative, DNA fragment, RNA fragment, DNA fragment derivative, RNA fragment derivative, naturally-derived drug, virus particle, bacterium particle, virus component, yeast component, blood cell, blood cell component, bacterium, bacterial component, natural or synthetic lipid, synthetic drug, poison, environmental pollutant, polymer, polymer particle, glass particle, plastic particle, polymer membrane and the like.

Among them, preferred substances to be labeled are antibody, protein, peptide, nucleotide, hormone, saccharide, lipid, vitamin, alkaloid, antibiotic and the like. Specific examples of the protein and peptide include, for example, immunoglobulins such as IgG, IgA, IgM, IgD and IgE, monoclonal antibodies directed to various proteins or membrane antigens of leucocyte, enzymes such as peroxidase, glucose oxidase, and alkaline phosphatase, and specific examples of the nucleotide include, for example, DNA, RNA, synthetic oligonucleotides, synthetic polynucleotides, ATP, CPT, GTP, TTP, UTP, dATP, dCTP, dGTP, dTTP, dUTP, ddATP, ddCTP, ddGTP, ddTTP, ddUTP, derivatives thereof. Specific examples of the saccharide include, for example, polysaccharides such as glycogen, starch and mannan, oligosaccharides and monosaccharides such as glucose and mannose, and specific examples of the lipid include, for example, phosphatidylcholine, phosphatidylethanolamine, fats, aliphatic acids. Examples of the hormone include, for example, peptide hormones such as insulin, growth hormones, epidermal growth factor, oxytocin, vasopressin and secretin, steroid hormones such as androgen and estrogen, catecholamines such as adrenaline and noradrenaline, and specific examples of the vitamin include, for example, vitamin A, vitamin B (B1, B2, B6, B12 and the like), vitamin C, vitamin D, vitamin E, biotin, folic acid. Specific examples of the alkaloid include, for example, opium alkaloids, tropane alkaloids such as atropine, indole alkaloids such as vinblastine, isoquinoline alkaloids such as coptis rhizome, and specific examples of the antibiotic include penicillin, cephalosporin, kanamycin, erythromycin. Among these substances to be labeled, substances that can be used for diagnosis (referred to as "diagnostic substances" in the specification, e.g., antibodies, proteins, peptides and the like) are preferred substances to be labeled.

Various techniques for introducing a fluorescence-labeling agent into a substance to be labeled are known, and when the compounds of the present invention are used as fluorescence-labeling agents, it is possible to appropriately select and use any means available to those skilled in the art. For example, a functional group in a substance to be labeled such as amino group and hydroxyl group can be directly bound to a reactive substituent such as carboxyl group and active ester group in the compounds of the present invention through an ionic bond or covalent bond, or after chemical modification such as introduction of a linker into a part of a substance to be labeled, the resulting product can be reacted with the compounds of the present invention. Alternatively, it is also possible to label a single-stranded DNA or RNA via a hydrogen bond with a base of a nucleic acid, or by intercalation into double-stranded DNA. The labeled substance after the reaction can be purified by commonly used separation techniques such as chromatography, electrophoresis, recrystallization and washing.

When the compounds of the present invention are used for DNA analysis, the compounds of the present invention can be incorporated into a probe or primer, for example, according to the method described by Ruth (Jerry L. Ruth, DNA, 3, 128 (1984)). The method of reacting a hydrophilic polyfunctional polymer such as proteins with a dye compound having a reactive substituent (e.g., active ester, isothiocyanate, iodoacetyl and the like) for labeling can be readily performed, for example, according to the method disclosed in U.S. Pat. No. 5,569,587. A dye having a carboxyl group that is not converted to an active ester can be labeled, for example, by the method described in Japanese Patent Unexamined Publication No. 6-222059.

Further, for example, an anti-tumor antibody can be labeled with the compound of the present invention and the labeled antibody can be brought into contact with a tissue or organ to prove existence of cancer cell or cancer tissue. For diagnosis, a tissue slice can be fixed by an appropriate method such as the paraffin method and observed under a microscope, or a tissue in vivo can be immunochemically stained and observed by using an endoscope. Recently, various fluorescence imaging methods using near infrared-ray fluorescent substances have been proposed (e.g., Japanese Patent Unexamined Publication No. 9-309845; J. Neurosurg., 87, pp. 738–745, 1997; Iyoh Denshi to Seitai Kogaku (Electrons for Medical Use and Bioengineering), 34, pp.316–322, 1996 and the like), and the compounds of the present invention can be used as diagnostic agents utilizing such fluorescence imaging methods.

When diagnostic substances labeled with the compounds of the present invention (e.g., labeled antibodies and the like) are used as diagnostic agents, they are preferably prepared in the form of a pharmaceutical composition by using one or more kinds of additives for pharmaceutical preparations. For example, a pharmaceutical composition in the form of solid, solution or the like can be prepared by using suitable additives for pharmaceutical preparations such as buffering agents, dissolving aids, pH modifiers, excipients, and preservatives. Those skilled in the art can appropriately choose a form of a pharmaceutical composition suitable for diagnosis or treatment as well as a method for preparation thereof. Furthermore, it is also possible to use the compounds of the present invention as fluorescence contrast media, which are administered into a blood vessel to visualize information in vivo (e.g., existence of cancer tissue and the like).

Methods for preparing the compounds of the present invention are not particularly limited, and they can be prepared via various synthetic routes. The compounds represented by the general formula (VII) can be prepared by applying a reaction well known as the Fischer's indole synthesis. The Fischer's indole synthesis is described in various publications. As for reaction conditions (temperature, solvent, time, reaction agent and the lie), R. J. Sudborg, "The Chemistry of Indoles", Academic Press, New York, 1970 and the reference cited therein can be referred to. For preparation of the compounds of the present invention, a higher reaction temperature is often required compared with usual indole or indolenine synthesis, however, reaction temperature can be appropriately chosen by those skilled in the art.

For preparation of the compounds represented by the general formula (VII), a coupling reaction of an aromatic compound or acetylene can be applied to an indolenine introduced with a leaving group such as a halogen. As for coupling reaction, "Cross-Coupling Reaction of Organic Boron Compound Using Palladium Catalyst" described in Chemical Review, vol. 95, p.2457 (1995) and references cited therein can be referred to, and the reaction known as Heck reaction described in Journal of Organic Chemistry, vol. 55, p.63 (1990) can be applied to easily produce a target substance. A compound represented by the general formula (VI) can be synthesized by treating a compound represented by the general formula (VII) with any of various alkylating agents.

Dyes represented by the general formulas (I) to (V) can be synthesized from a compound represented by the general formula (VI) by using a known method. As for reaction conditions (temperature, solvent, time, reaction agents and the like), explanations are given in F. M. Harmer, "Heterocyclic Compounds—Cyanine Dyes and Related Compounds", John Wiley and Sons, New York, London, 1964; D. M. Sturmer, "Heterocyclic Compounds—Special Topics in Heterocyclic Chemistry", Chapter 18, Section 14, 482 to 515 pages and the like.

Methods for preparation of typical compounds are specifically described in the examples of the specification. Accordingly, those skilled in the art can prepare any compound falling within the scope of the aforementioned general formulas by referring to the specific explanations in the following example and appropriately choosing a compound as a starting material, reaction conditions, reagents and the like, and applying modification or alteration to the methods described in the examples as required. However, methods for preparing the compounds of the present invention represented by the aforementioned general formulas are not particularly limited, and it should be understood that those prepared by any methods fall within the scope of the present invention.

EXAMPLES

Example 1

Synthesis of Compound VII-43

5-Bromo-2-hydrazinopyridine (10 g) and 3-methyl-2-butanone (20 ml) were mixed and allowed to react at 80° C. for 15 minutes. After evaporation of excess 3-methyl-2-butanone, the reaction mixture was added with 1,4-butanediol (15 ml) and allowed to react for 5 hours with heating at 230° C. The reaction mixture was cooled and subjected to silica gel column chromatography without treatment. The solvent was evaporated from the fraction containing the target substance, and then the residue was crystallized from hexene/ethyl acetate to obtain Compound VII-43 as light brown crystals.

Yield: 2.0 g (15.7%) Melting point: 132–134° C. H-NMR (CDCl$_3$), δ 8.50 (d, 1H), 7.70 (d, 1H), 2.40 (s, 3H), 1.86 (s, 6H)

Example 2

Syntheses of Compounds VII-13 to VII-31 and Compounds VII-34 and VII-35

Compounds VII-13 to VII-31 and Compounds VII-34 and VII-35 were synthesized from corresponding hydrazinopyridines under the same conditions as those for Compound VII-43 though they were obtained in a low yield. The structures of the compounds were verified based on values obtained in mass spectrometry and elemental analysis.

Example 3

Synthesis of Compound VII-1

Compound VII-1 was synthesized by the synthetic route descried below.

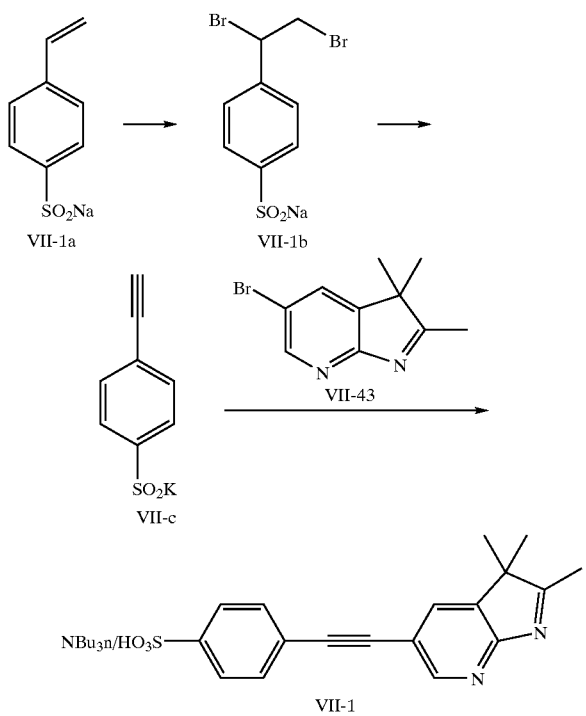

Example 4

Syntheses of Compound VII 2 and Compound VII-3

Compounds VII-2 and VII-3 were synthesized by the synthetic route described below.

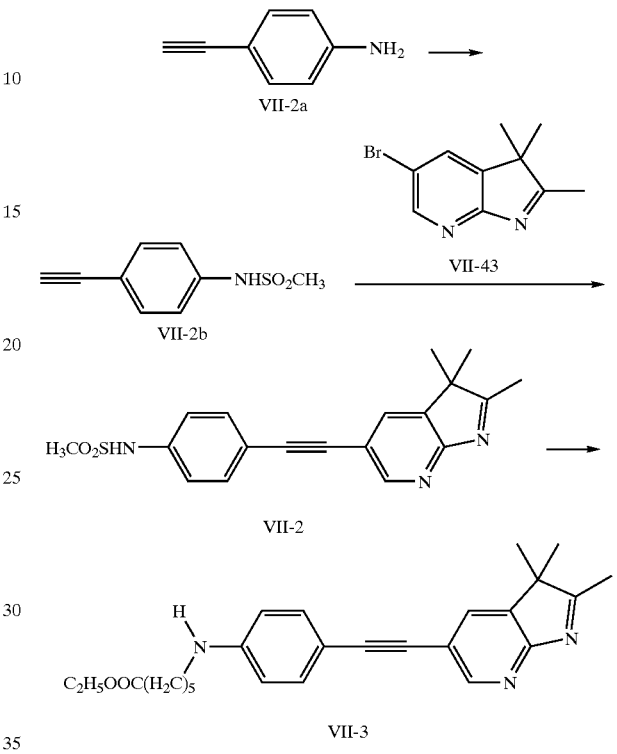

(1) Synthesis of Compound VII-1b

Compound VII-1a (121 g) was suspended in acetic acid (3 L) and added dropwise with bromine (94 g) under water cooling over 2 hours. The reaction mixture was further stirred for 1 hour, and then the crystals were collected by filtration to obtain Compound VII-1b. Yield: 182.3 g (62%). H-NMR (D$_2$O), δ 7.83 (d, 2H), 7.70 (d, 2H), 5.42 (t, 1H), 4.20 (d, 2H)

(2) Synthesis of Compound VII-1c

Compound VII-1b (100 g) was added to 20% aqueous potassium hydroxide and the mixture was allowed to react at 90° C. One hour after the reaction was started, the reaction mixture became uniform. The reaction was further continued for 2 hours. Then, after the reaction mixture was stirred with ice cooling for 1 hour, crystals of the target substance Compound VII-1c deposited. Yield: 41 g (68%). H-NMR (DMSO-d$_6$) δ 7.61 (d, 2H), 7.43 (d, 2H), 4.20 (s, 1H)

(3) Synthesis of Compound VII-1

Compound VII-43 (8.3 g) and Compound VII-1c (5.0 g) were dissolved in DMF (50 ml) under a nitrogen flow, added with potassium carbonate (6.2 g) and tetrakistriphenylphosphine palladium (0.52 g), and the mixture was allowed to react at 90° C. for 6 hours. When ethylene acetate was added to the reaction mixture, crystals containing mineral salt precipitated, and then the crystals were collected by filtration. When the crystals were added with water (200 ml), chloroform (200 ml), hydrochloric acid (5 ml) and tributylamine (10 ml) for separation, the target substance was extracted in the chloroform layer as tributylamine salt. The chloroform layer was washed twice with water and then concentrated. The residue was crystallized from ethyl acetate/hexane to obtain Compound II-1. Yield: 7.0 g (89%). H-NMR (DMSO-d$_6$) δ 8.50 (d, 1H), 8.05 (d, 1H), 7.60 (d, 2H), 7.45 (d, 2H), 2.35 (s, 3H), 1.35 (s, 6H)

(1) Synthesis of Compound VII-2b

Compound VII-2a (11.7 g) was dissolved in a two-layer system of ethyl acetate (100 ml) and aqueous sodium hydrogencarbonate (100 ml), and added with pyridine (8 ml). The mixture was then added dropwise with methanesulfonyl chloride (22 g), and allowed to react for 8 hours under ice cooling. The ethyl acetate layer was separated and washed with saturated aqueous sodium hydrogencarbonate. The ethyl acetate was evaporated and the reside was recrystallized from a small amount of ethyl acetate to obtain Compound VII-2b. Yield: 16.6 g (85%). H-NMR (DMSO-d$_6$) δ 10.02 (s, 1H), 7.41 (d, 2H), 7.18 (d, 2H), 4.10 (s, 1H), 3.08 (s, 3H)

(2) Synthesis of Compound VII-2

Compound VII-48 (2.6 g) and Compound VII-2b (3.0 g) were dissolved in DMF (40 ml) under a nitrogen flow, and the mixture was added with potassium carbonate (4.1 g) and tetrakistriphenylphosphine palladium (0.38 g), and then allowed to react at 90° C. for 2.5 hours. The reaction mixture was extracted with chloroform (200 ml), and the extract was concentrated. The residue was crystallized from ethyl acetate/hexane to obtain crude crystals of Compound VII-2. The crude crystals were further recrystallized from ethyl acetate to obtain Compound VII-2. Yield: 3.5 g (91%). H-NMR (DMSO-d$_6$) δ 9.92 (s, 1H), 8.50 (d, 1H), 8.05 (d, 1H), 7.52 (d, 2H), 7.25 (d, 2H), 3.10 (s, 3H), 2.35 (s, 3H), 1.35 (s, 6).

(3) Synthesis of Compound VII-8

Compound VII-2 (0.51 g) was dissolved in DMF (7 ml), and the solution was added with ethyl 6-bromohexanoate (0.32 g) and potassium carbonate (0.60 g) and then the mixture was allowed to react at 55° C. for 5 hours. The reaction mixture was extracted with ethyl acetate, and the extract was concentrated and then subjected to silica gel column chromatography to obtain Compound VII-3. Yield: 0.46 g (64%). H-NMR (CDCl$_3$) δ 8.52 (d, 1H), 8.05 (d, 1H), 7.58 (d, 2H), 7.42 (d, 2H), 4.02 (dd, 2H), 3.65 (m, 2H), 3.00 (s, 3H), 2.35 (s, 3H), 2.20 (t, 2H), 1.50–1.30 (m, 12H), 1.18 (t, 3H)

Example 5

Syntheses of Compound VII-4 and Compound VII-5

Compound VII-4 and Compound VII-5 were obtained by using m-aminophenylacetylene as a starting material with the synthetic conditions for Compound VII-2 and Compound VII-3.
Compound VII-4: H-NMR (DMSO-d$_6$) δ 9.92 (s, 1H), 8.50 (d, 1H), 8.05 (d, 1H), 7.42–7.20 (m, 4H), 3.00 (s, 3H), 2.30 (s, 3H), 1.25 (s, 6H)
Compound VII-5: H-NMR (CDCl$_3$) δ 8.52 (d, 1H), 8.05 (d, 1H), 7.38–7.10 (m, 4H), 4.00 (dd, 2H), 3.60 (m, 2H), 2.98 (s, 3H), 2.30 (s, 3H), 2.20 (t, 2H), 1.50–1.30 (m, 12H), 1.18 (t,3H).

Example 6

Synthesis of Compound VII-6

Compound VII-43 (2.4 g), potassium carbonate (3.5 g), triphenylphosphine (0.31 g) and cuprous iodide (0.12 g) were added to diethylene glycol dimethyl ether (20 ml) and water (20 ml) under a nitrogen flow, and then the mixture was stirred at 25° C. for 30 minutes. Then, the reaction mixture was added and propargyl alcohol (1.5 ml). The reaction temperature was raised to 80° C., and the reaction mixture was allowed for 16 hours at the same temperature. The reaction mixture was filtered through Cerite, and the filtrate was made acidic with addition of hydrochloride acid and washed with ethyl acetate. When the acidic aqueous layer was made to be pH 8.0 with addition of aqueous sodium hydroxide and the aqueous layer was mixed with chloroform and separated, the target substance was extracted in the chloroform layer. The chloroform was evaporated and the residue was recrystallized from ethyl acetate to obtain Compound VII-6. Yield: 1.7 g (80%) H-NMR (DMSO-d$_6$) δ 8.52 (d, 1H), 7.62 (d, 1H), 4.52 (m, 2H), 2.33 (s, 3H), 1.30 (s, 6H)

Example 7

Synthesis of Compound VII-7

A reaction was performed by using 2-methyl-3-butyn-2-ol instead of propargyl alcohol used in the synthesis of Compound VII-6 under the same conditions as the synthesis of Compound VII-6 to synthesize Compound VII-7. The structure was verified by mass spectrometry.

Example 8

Synthesis of Compound VII-8

Compound VII-43 (1.2 g) and benzo[b]furan-2-boronic acid (1.2 g) were dissolved in DMF (15 ml) under a nitrogen flow, and the mixture was added with cesium carbonate (3.2 g) and tetrakistriphenylphosphine palladium (0.29 g) and then allowed to react at 100° C. for 3 hours. The reaction mixture was extracted with ethyl acetate and the extract was concentrated. The residue was recrystallized from ethyl acetate to obtain Compound VIII-8. Yield: 1.0 g (73%). H-NMR (CDCl$_3$) δ 8.95 (d, 1H), 8.02 (d, 1H), 7.62 (d, 1H), 7.54 (d, 1H), 7.36–7.22 (m, 2H), 7.10 (s, 1H), 2.40 (s, 3H), 1.38 (s, 6H)

Example 9

Syntheses of Compounds VII-9 and VII-10

When a reaction was performed by using 2-furanboronic acid or 2-thiopheneboronic acid instead of the benzo[b]furan-2-boronic acid used in the synthesis of Compound VII-8 under the same conditions as those for the synthesis of Compound VII-8, Compound VII-9 and Compound V-10 were obtained. Structure of each was verified by mass spectrometry.

Example 10

Synthesis of Compound VII-12

Compound VII-11 was synthesized by following the route shown below.

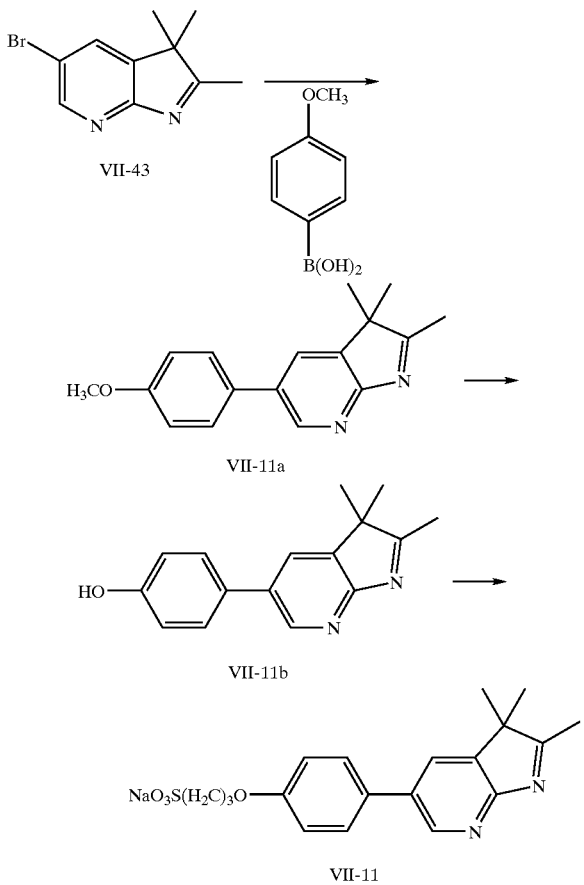

(1) Synthesis of Compound VII-11a

A reaction was performed by using 4-methoxyphenylboronic acid instead of the benzo[b]furan-2-boronic acid used in the synthesis of Compound VII-8 under the same conditions as those for the synthesis of Compound VII-8 to obtained Compound VII-11a. H-NMR (DMSO-d$_6$) δ 8.59 (d, 1H), 8.08 (d, 1H), 7.62 (d, 2H), 7.02 (d, 2H), 3.80 (s, 3H), 2.30 (s, 3H), 1.38 (s, 6H)

(2) Synthesis of Compound VII-11b

Compound VII-11a (1.0 g) was dissolved in 47% aqueous hydrogen bromide (15 ml) and allowed to react at 130° C. for 2 hours. The reaction mixture was neutralized with 10% aqueous sodium hydroxide with ice cooling and extracted with chloroform. The chloroform was evaporated, and the residue was recrystallized from isopropyl alcohol/hexane to obtain Compound VII-11b. Yield: 0.85 g (90%).

The structure was verified by mass spectrometry.

(3) Synthesis of Compound VII-11

Compound VII-11b (0.22 g) was dissolved in DMF (10 ml) and added with sodium hydride (35 mg) and propane-sulfone (0.1 g) with ice cooling, and then the mixture was allowed to react under ice cooling for 10 minutes and at room temperature for 20 minutes. The reaction mixture was added with isopropyl alcohol and a small amount of ethyl acetate to deposit crystals to obtain Compound VII-11. Yield: 0.30 g (87%).

The structure was verified by mass spectrometry.

Example 11

Synthesis of Compound VII-12

A reaction was performed by using p-tolylboronic acid instead of the benzo[b]furan-2-boronic acid used in the synthesis of Compound VII-8 under the same conditions as those for the synthesis of Compound VII-8 to obtain Compound VII-12. H-NMR (DMSO-d$_6$) δ 8.59 (d, 1H), 8.12 (d, 1H), 7.62 (d, 2H), 7.30 (d, 2H), 3.80 (s, 3H), 2.38 (s, 3H), 2.30 (s, 3H), 1.35 (s, 6H).

Example 12

Synthesis of Compound VII-42

5-Chloro-2-hydrazinopyridine (35 g) and 3-methyl-2-butanone (100 ml) were mixed and allowed to react at 100° C. for 30 minutes. After evaporation of excess 3-methyl-2-butanone, the reaction mixture was added with 1,4-butanediol (100 ml) and allowed to react for 5 hours with heating at 240° C. The reaction mixture was cooled and subjected to silica gel column chromatography without treatment. The solvent was evaporated from the fraction containing the target substance, and then the residue was crystallized from hexane/ethyl acetate to obtain Compound VII-42 as light brown crystals. Yield: 14.0 g (29.5%). Melting point: 118–120° C. H-NMR (CDCl$_3$) δ 8.50 (d, 1H), 7.70 (d, 1H), 2.40 (s, 3H), 1.36 (s, 6H)

Example 13

Synthesis of Compound VII-46

2,6-Difluoropyridine (25 g), isopropyl alcohol (100 ml) and hydrazine hydrate (40 ml) were mixed and refluxed with heating for 3 hours. The isopropyl alcohol was evaporated under reduced pressure, and the residue was added with water. The deposited crystals were collected by filtration, washed with water and dried to obtain 6-fluoro-2-hydrazinopyridine (21.2 g, yield: 76.8%). Coloration was observed during drying, and accordingly, the product was used for the next reaction immediately after the drying.

6-Fluoro-2-hydrazinopyridine (10 g) and 3-methyl-2-butanone (20 ml) were mixed and allowed to react at 80° C. for 15 minutes. After evaporation of excess 3-methyl-2-butanone, the reaction mixture was added with ethylene glycol (20 ml) and allowed to react for 5 hours with heating at 220° C. The reaction mixture was cooled and added with water and ethyl acetate to extract the target substance in the organic layer. The ethyl acetate was evaporated and the residue was subjected to silica gel column chromatography. The solvent was evaporated from the fraction containing the target substance, and then the residue was crystallized from hexane/ethyl acetate to obtain Compound VII-46. Yield: 3.2 g (22.8%). Melting point: 88–90° C.

Example 14

Synthesis of Compound VII-64

Compound VII-42 (4.5 g), DMF (40 ml), 3-hydroxy-1-propanethiol (4.0 g) and potassium t-butoxide (3.9 g) were mixed and refluxed with heating under a nitrogen flow for 5 hours. After completion of the reaction, DMF was evaporated under reduced pressure, and the resulting brown oily substance was purified by silica gel column chromatography to obtain the target substance as a light yellow oily substance. Yield 1.0 g (17.9%) H-NMR (CDCl$_3$) δ 8.88 (d, 1H), 7.58 (d, 1H), 4.83 (b, 1H), 3.77 (t, 2H), 3.05 (t, 2H), 3.36 (s, 3H), 1.90 (m, 2H), 1.36 (s, 6H)

Example 15

Synthesis of Compound VII-72

(1) Synthesis of 6-mercaptohexanoic acid ethyl ester

8-Bromohexanoic acid ethyl ester (250 g), thiourea (102.3 g), and isopropanol alcohol (500 ml) were mixed and refluxed with heating for 10 hours. After cooling, isopropanol alcohol was evaporated under reduced pressure and the residue was added with hexane (500 ml) and stirred. The hexane layer was removed by decantation, and the residue was added with potassium carbonate (400 g), ethyl acetate (1 L), ethanol (1 L) and water (2 L), and then the mixture was allowed to react at 75° C. under a nitrogen flow for 6 hours. After completion of the reaction, the reaction mixture was added with ethyl acetate (1 L), and the layers were separated. The organic layer was concentrated and purified by silica gel column chromatography. The target substance was obtained as a colorless oily substance. Yield: 159 g (80.5%).

(2) Synthesis of Compound VII-72

Compound VII-42 (5 g) was dissolved in DMF (40 ml) and added with 6-mercaptohexanoic acid ethyl ester (8 g). This solution was added with potassium acetate (5.5 g) and refluxed with heating under a nitrogen flow for 8 hours. The reaction mixture was purified by silica gel column chromatography to obtain Compound VII-72 as a colorless oily substance. Yield: 2.6 g (30.0%). H-NMR (CDCl$_3$) δ 8.57 (d, 1H), 8.40 (d, 1H), 4.12 (q, 2H), 2.90 (m, 4H), 2.31 (s, 3H), 2.28 (m, 2H), 1.63 (m, 4H), 1.33 (s, 6H), 1.25 (t, 3H)

A compound of the general formula (VI) can be synthesized by reacting a compound of the general formula (VII) with an alkylating agent. However, in the synthesis, alkylation of indolenine nitrogen may sometimes be simultaneously occurred together with the intended alkylation on the nitrogen of the pyridine. Purity of a target substance can be increased by washing with hot isopropyl alcohol or ethyl acetate for most of compounds. Compounds for which washing is less effective may be subjected to the subsequent reaction as a mixture. When dyes are formed, crystallizability of target substances often increases, and in most of dyes, impurities derived from indolenine nitrogen-alkylated compounds can be removed by recrystallization. In the following examples, it was difficult to obtain compounds of the general formula (VI) in a high purity, and therefore, structures of target substances were verified by mass spectrometry.

Example 16

Synthesis of Compound VI-1

Compound VII-1 (1 g) was dissolved in acetone (2 ml) and added with methyl iodide (2 ml), and then the mixture was refluxed with heating for 6 hours. The crystals deposited from the reaction mixture were washed with isopropyl alcohol to obtain amorphous Compound VI-1. Yield: 0.64 g (70%) Mass (posi): m/e=355

Example 17

Synthesis of Compound VI-2

Compound VII-1 (1 g) was dissolved in acetone (2 ml) and added with 2-methylpropanesulfone (2 ml), and then the mixture was refluxed with heating for 5 hours. The crystals deposited from the reaction mixture were washed with acetone to obtain Compound VI-2. Yield: 0.71 g (65%) Mass (posi): m/e=476

Example 18

Synthesis of Compound VI-7

Compound VII-1 (1 g) was dissolved in acetone (2 ml) and added with ethyl 6-bromohexanoate (2 ml), and then the mixture was refluxed with heating for 8 hours. When ethyl acetate was added to the reaction mixture, oily precipitates were formed. The supernatant ethyl acetate was removed by decantation and the residue was washed several times with ethyl acetate and dried under reduced pressure to obtain amorphous Compound VI-7. Yield: 0.70 g (76%) Mass (nega): m/e=483

Other compounds represented by the general formula (VI) were successfully synthesized according to the synthesis methods of Examples 16 and 18.

A compound represented by the formula (I) or the formula (II) can be generally synthesized by the methods shown in the following schemes.

Scheme (A)
Method for Synthesizing a Symmetric Cyanine

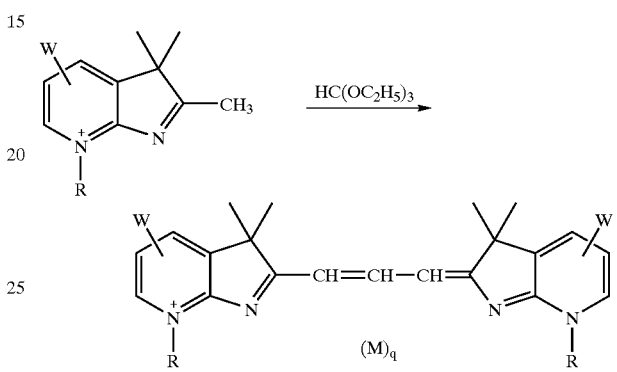

Scheme (B)
Method for Synthesizing an Asymmetric and Merocyanine

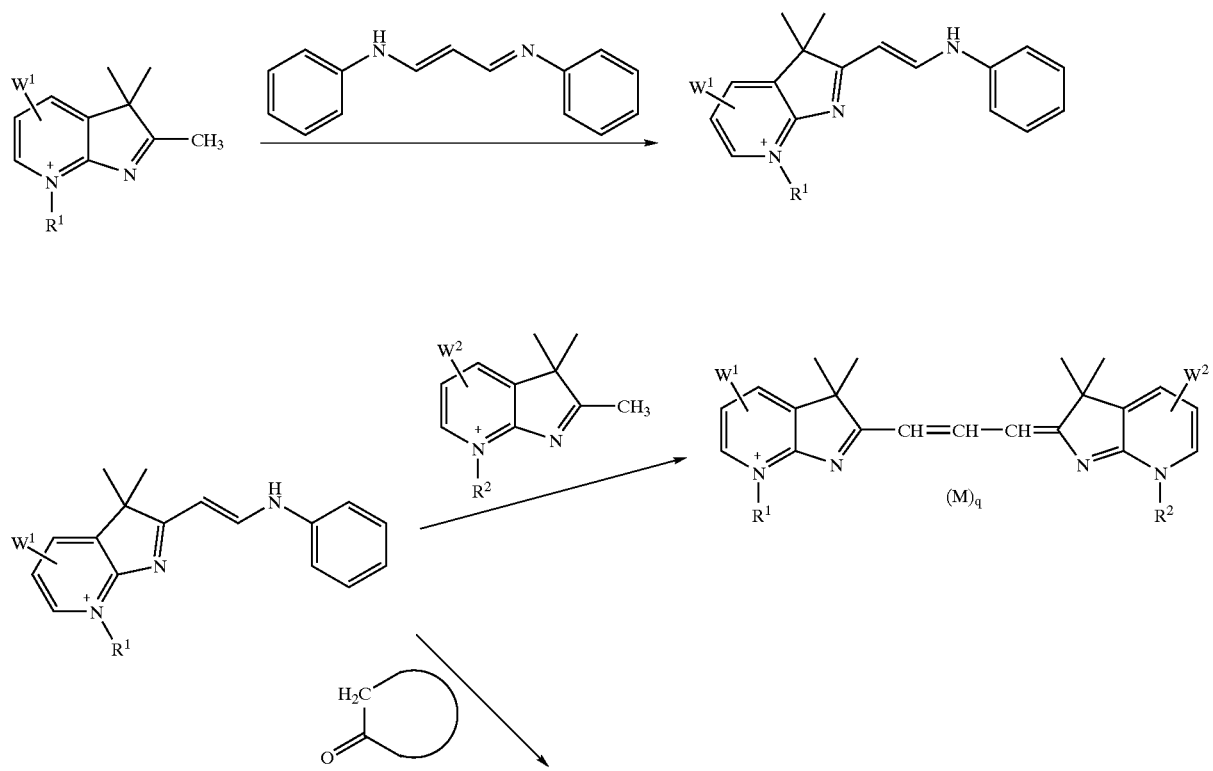

-continued

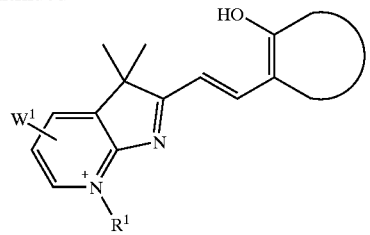

Example 19

Synthesis of Compound I-1

Compound I-1 was synthesized according to the route of Scheme (B). Compound VI-1 (0.35 g), N,N'-diphenylformamidine (0.6 g) and acetic anhydride (5 ml) were mixed and allowed to react at 90° C. for 1 hour. The reaction mixture was added with ethyl acetate (50 ml), and the deposited dye intermediate was separated. The resulting dye intermediate and Compound VI-7 (0.48 g) were dissolved in DMF (5 ml) and added with triethylamine (0.5 ml) and acetic anhydride (0.2 ml), and the mixture was allowed to react at room temperature for 2 hours. The reaction mixture was added with ethyl acetate to produce oily residue. After the supernatant ethyl acetate was removed, the residue was purified by silica gel chromatography to separate ethyl ester of Compound I-1.

The resulting ester compound was dissolved in 5% aqueous lithium hydroxide and allowed to react at room temperature for 30 minutes to produce the target Compound I-1. The reaction mixture was added with water, chloroform, hydrochloric acid and tributylamine, and the layers were evaporated. The chloroform layer containing the target substance was washed twice with water and concentrated, and the residue was added with ethyl acetate to obtain tributylamine salt of Compound I-1. The tributylamine salt was dissolved in methanol and added with potassium acetate to obtain potassium salt of Compound I-1, and the resulting product was recrystallized from methanol to obtain Compound I-1 at an HPLC purity of 99% or higher. Yield: 120 mg (11%). Mass (nega): m/e=861 Absorption maximum (methanol): 650 nm Molecular extinction coefficient: 238000 Melting point: >300° C.

Example 20

Synthesis of Compound I-2

A reaction was performed under the same conditions as those in Example 19 except that Compound I-2 was used instead of Compound I-1 used in the synthesis of Compound I-1 to obtain Compound I-2. Mass (nega): m/e=1015 Absorption maximum (methanol): 651 nm Molecular extinction coefficient: 238000

Example 21

Synthesis of Compound I-3

A carboxylic acid derivative of Compound I-3 was synthesized under the same conditions as those for the synthesis of Compound I-2. The resulting carboxylic acid derivative was dissolved in a mixed solvent of DMF and pyridine and added with N,N'-disuccinimdyl carbonate, and then the mixture was allowed to react at 40° C. for 2 hours. The reaction mixture was added with isopropyl alcohol and the resulting crystals were collected by filtration. The crystals were purified by gel filtration (Sophadox G 10) to obtain Compound I-3. Mass (nega): m/e=1031 Absorption maximum (methanol): 651 nm Molecular extinction coefficient: 218000

Example 22

Synthesis of Compound I-11

Compound I-11 was synthesized by following the route shown below.

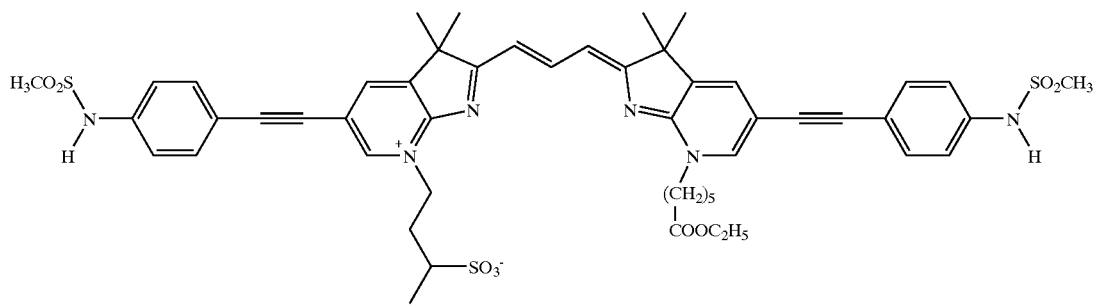

I-11a

| Sulfoalkylation

-continued

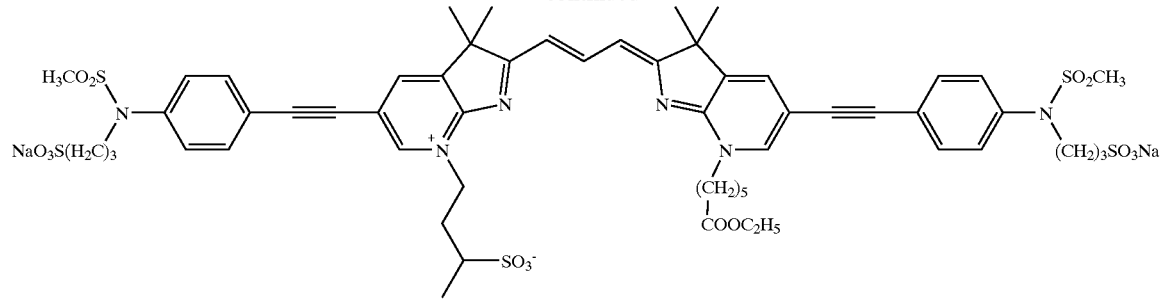

I-11b

↓ Hydrolysis of ester
↓ Salt exchange

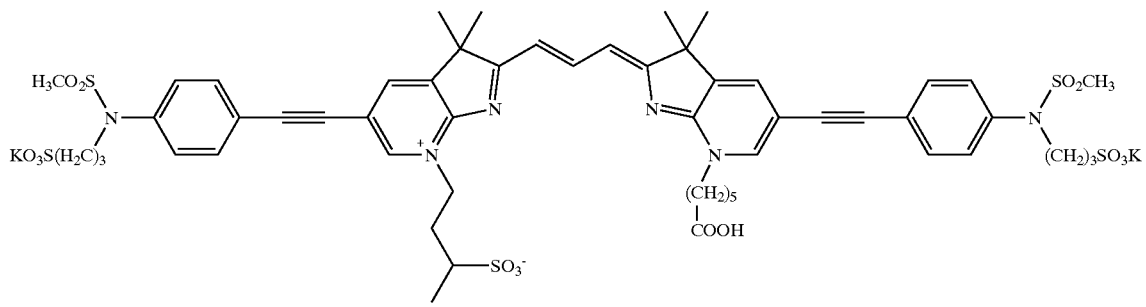

I-11

Compound I-11a was obtained by using Compound VI 0 and Compound VI-12 according to the aforementioned method. Compound I-11a (45 mg) was dissolved in DMF (4 ml) and added with potassium carbonate (0.2 g) and propanesulfone (0.5 ml), and then the mixture was allowed to react at 50° C. for 8 hours to attain sulfoalkylation. The reaction mixture was added with isopropyl alcohol and the resulting crystals were collected by filtration. The crystals were dissolved in water and added with chloroform, tributylamine and hydrochloric acid and the layer was separated. The chloroform layer was concentrated under reduced pressure, and the resulting oily residue was added with 6% aqueous lithium hydroxide and stirred at room temperature for 1 hour to perform hydrolysis of the ester. Then, the reaction mixture was added with chloroform, tributylamine and hydrochloric acid an the layers were separated. The chloroform layer was concentrated and the resulting oily reside was added with a methanol solution of potassium acetate to obtain Compound I-11 as crystals. Yield: 40 mg(69%) Mass (nega): m/e=1248 Absorption maximum (methanol): 650 nm Molecular extinction coefficient: 235000 Melting point: >300° C.

Example 23

Synthesis of Compound I-12

Compound I-12 was synthesized via the same synthetic route and under the same conditions as those for Compound I-11 by using Compound VII-4 as a starting material. Mass (nega): m/e=1234 Absorption maximum (methanol): 649 nm Molecular extinction coefficient: 233000 Melting point: >300° C.

Example 24

Synthesis of Compound I-13

Compound I-13 was synthesized by the synthetic route described below by using Compound VII-4 and Compound VII-5 as starting materials.

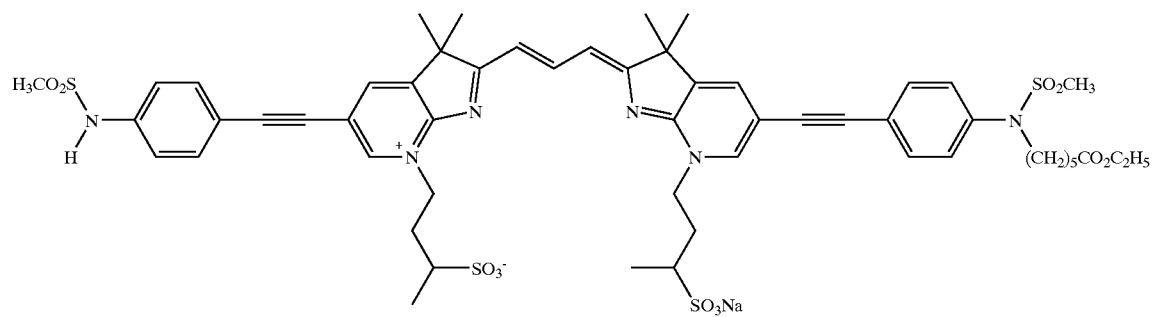
Sulfoalkylation ↓
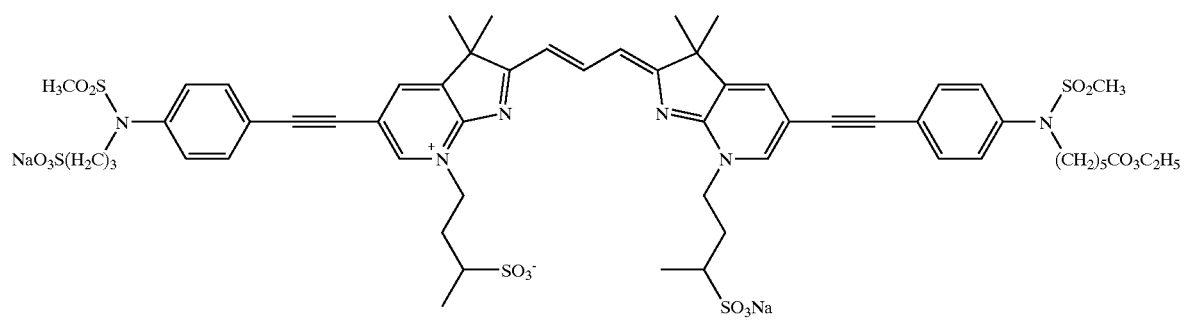
Hydrolysis of ester ↓
Salt exchange ↓
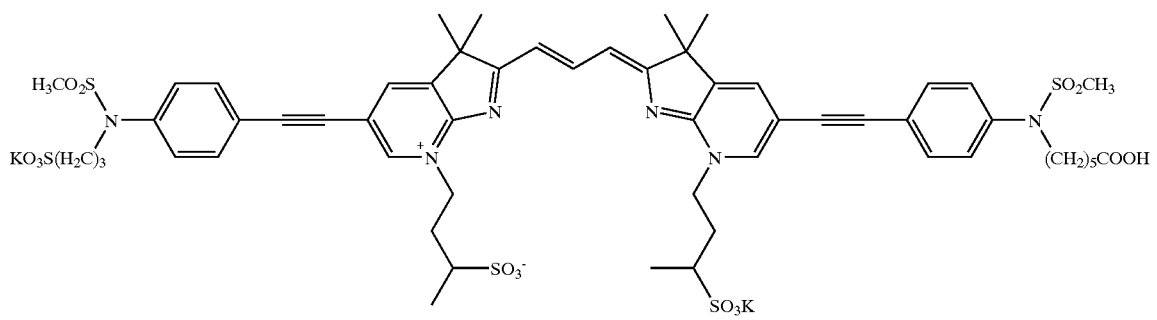

The synthetic conditions for Compound I-13 were similar to those for Compound I-11. Mass (nega): m/e=1262 Absorption maximum (methanol): 649 nm Molecular extinction coefficient: 233000 Melting point: >300° C.

Other dyes were also successfully synthesized according to the methods of Examples 19 and 24.

Example 25

Comparison of Relative Fluorescence Quantum Yield

Relative fluorescence quantum yields of the compounds of the present invention are shown in Table 1. Measurement and calculation of relative quantum yield were performed according to the method described in Journal of Chemical Society, Faraday Trans., 92, 4917–4925 (1996). The structures of the conventional cyanine dye used as comparative dyes are shown below. As clearly shown by the results in Table 1, the dyes of the present invention are suitable for excitation by using an inexpensive helium-neon laser light source (633 nm), and their fluorescence intensity is two to three times stronger than that of the conventional dyes.

Comparative dye 1

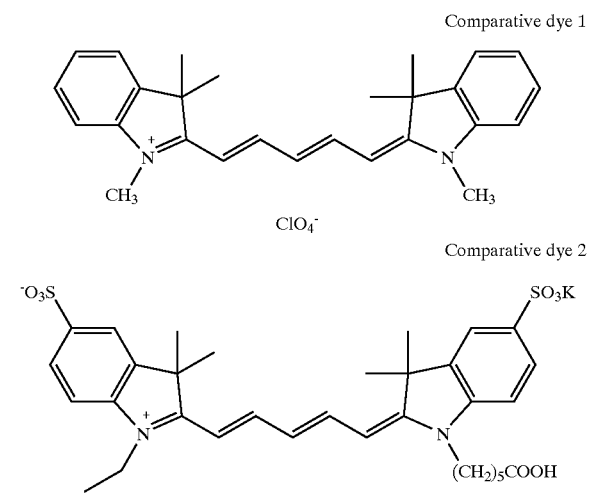

Comparative dye 2

TABLE 1

| Compound No. | Absorption maximum (nm) | Fluorescence maximum (nm) | Relative fluorescence quantum yield |
|---|---|---|---|
| Comparative Compound 1 | 641 | 660 | 0.21 |
| Comparative Compound 2 | 645 | 664 | 0.27 |
| I-1 | 649 | 669 | 0.68 |
| I-2 | 649 | 669 | 0.68 |
| I-8 | 649 | 669 | 0.67 |
| I-11 | 651 | 672 | 0.63 |
| I-12 | 650 | 671 | 0.62 |
| I-13 | 651 | 672 | 0.63 |
| I-14 | 649 | 671 | 0.63 |
| I-15 | 650 | 671 | 0.62 |
| I-16 | 635 | 652 | 0.65 |
| I-17 | 634 | 651 | 0.64 |
| I-18 | 635 | 652 | 0.63 |
| I-21 | 643 | 668 | 0.61 |
| I-22 | 656 | 676 | 0.61 |
| I-23 | 646 | 662 | 0.63 |
| I-24 | 633 | 651 | 0.64 |
| I-25 | 630 | 547 | 0.63 |
| I-26 | 650 | 667 | 0.59 |
| I-27 | 635 | 650 | 0.69 |
| I-28 | 634 | 650 | 0.7 |
| I-31 | 632 | 648 | 0.72 |
| I-36 | 625 | 640 | 0.6 |
| I-44 | 623 | 635 | 0.58 |
| I-50 | 640 | 660 | 0.58 |
| I-54 | 638 | 662 | 0.64 |

Measurement method (1) Concentration of ethanol solution of dye was adjusted so that the solution had absorbance of 0.1 at 620 nm.
(2) Fluorescence spectrum was measured at an excellent wavelength of 620 nm.
(3) Area value of fluorescence spectrum was calculated.
(4) Relative value was calculated based on the area value of Crystal Violet of which absolute fluorescence quantum yield was known ($\Phi f=0.54$).

Example 26

Evaluation of Aggregation Characteristic

Compounds of the present invention were dissolved in 50 mM Tris-HCl buffer (pH 8.0), 4×SSC (67 mM NaCl, 67 mM sodium citrate), 1 M Church-phosphate buffer (0.5 M $Na_2HOP_4/H_3PO_4$, pH 7.2) and 1 M aqueous sodium chloride, and absorption spectrum patterns were evaluated. As a result, it was revealed that all of the dyes described in specific examples had a monomeric spectrum in an organic solvent as a main absorbance. In particular, Compounds I-1 to I-21 were absolutely free from aggregation which is observed for ordinary cyanine dyes.

Industrial Applicability

The compounds represented by the general formula (I), (II), (IV) and (V) of the present invention have properties of two to three-fold higher fluorescence intensity than conventional dyes and no aggregation tendency even in an aqueous medium at a high salt concentration, and thus they satisfy conditions as dyes for fluorescence-labeling. Therefore, they can be used as highly sensitive fluorescence-labeling agents for DNA sequencing or measurement of physiologically active substance or the like based on fluorescence immunoassay, or can be used as fluorescence contract media and the like that are administered into a blood vessel to visualize information in vivo. Furthermore, the compounds represented by the general formula (III), (IV) and (VII) are useful as synthetic intermediates for preparation of the aforementioned compounds.

What is claimed is:

1. A compound represented by the following general formula (IV):

General Formula (IV)

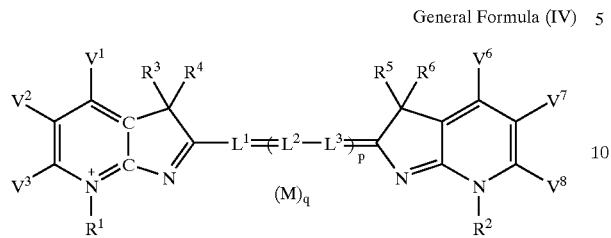

wherein $V^1$, $V^2$, $V^3$, $V^6$, $V^7$ and $V^8$ represent a hydrogen atom or a group selected from the group consisting of a halogen atom, an alkyl group, an alkenyl group, an alkynyl group, an aryl group, a heterocyclic group, cyano group, hydroxy group, nitro group, carboxyl group, an alkoxy group, an aryloxy group, a silyloxy group, a heterocyclyloxy group,, an acryloxy group, a carbamoyloxy group, an alkoxycarbonyloxy group, an aryloxycarbonyloxy group, an amino group (including an anilino group), an acylamino group, an aminocarbonylamino group, an alkoxycarbonylamino group, an aryloxycarbonyl-lamino group, a sulfamoylamino group, an alkylsulfonylamino group, an arylsulfonylamino group, a mercapto group, an alkylthio group, an arylthio group, a heterocyclylthio group, a suifamoyl group, an alkylsulfinyl group, an arylsulfinyl group, an alkylsulfonyl group, an arylsulfonyl group, an acyl group, an aryloxycaronyl group, an alkoycarbonyl group, a carbamoyl group, a phosphono group, a phosphonato group and a group that can form a covalent bond with a compound to be labeled (each of said group may be substituted), provided that $V^1$, $V^2$ and $V^3$ do not simultaneously represent a hydrogen atom, and provided that $V^1$ and $V^2$, $V^2$ and $V^3$, $V^6$ and $V^7$, and $V^7$ and $V^8$ may each independently form a saturated or unsaturated ring that may be substituted; $R^1$ and $R^2$ each independently represent a hydrogen atom or a group selected from the group consisting of an alkyl group, an aryl group and a heterocyclic group (each of said group may be substituted); $R^3$, $R^4$, $R^5$ and $R^6$ each independently represent an alkyl group that may be substituted, and $R^3$ and $R^4$, and $R^5$ and $R^6$ may each independently bind to each other to form a ring that may be substituted; $L^1$, $L^2$ and $L^3$ each independently represent a methine group that may be substituted; p represents 1, 2 or 3; M represents a counter ion; and q represents a number required to neutralize a charge of the molecule, wherein at least one of $V^1$, $V^2$ and $V^3$ is an aryl group substituted with a sulfo group or a salt thereof, a heterocyclic group substituted with a sulfo group or a salt thereof, or an alkynyl group substituted with a sulfo group or salt thereof.

* * * * *